US012669392B2

(12) United States Patent
Li et al.

(10) Patent No.: US 12,669,392 B2
(45) Date of Patent: Jun. 30, 2026

(54) METHOD FOR DETECTING THREE-DIMENSIONAL FORCE OF A FIBER-INTEGRATED MONOLITHIC CLAMP GUIDED BY METAL ADDITIVE MANUFACTURING

(71) Applicant: Wuhan University of Technology, Wuhan (CN)

(72) Inventors: Tianliang Li, Wuhan (CN); Haolei Fan, Wuhan (CN); Chen Zhao, Wuhan (CN); Mingchang Du, Wuhan (CN); Yongwen Zhu, Wuhan (CN)

(73) Assignee: Wuhan University of Technology, Wuhan (CN)

( * ) Notice: Subject to any disclaimer, the term of this patent is extended or adjusted under 35 U.S.C. 154(b) by 0 days.

(21) Appl. No.: 19/273,365

(22) Filed: Jul. 18, 2025

(65) Prior Publication Data

US 2025/0347570 A1     Nov. 13, 2025

(30) Foreign Application Priority Data

Oct. 14, 2024     (CN) .......................... 202411428571.5

(51) Int. Cl.
| | |
|---|---|
| *G01L 1/24* | (2006.01) |
| *A61B 17/00* | (2006.01) |
| *A61B 17/28* | (2006.01) |
| *G01K 11/3206* | (2021.01) |

(52) U.S. Cl.
CPC .............. *G01L 1/246* (2013.01); *A61B 17/28* (2013.01); *G01K 11/3206* (2013.01); *A61B 2017/00084* (2013.01); *A61B 2017/2808* (2013.01); *A61B 2562/0266* (2013.01)

(58) Field of Classification Search
CPC .................... G01L 1/246; A61B 17/28; A61B 2017/00084; A61B 2017/2808; A61B 2562/0266; G01K 11/3206
See application file for complete search history.

(56) References Cited

U.S. PATENT DOCUMENTS

| | | |
|---|---|---|
| 2011/0184406 A1 | 7/2011 | Selkee |
| 2022/0242383 A1 | 8/2022 | Camozzi |

FOREIGN PATENT DOCUMENTS

| | | | | |
|---|---|---|---|---|
| CN | 115839792 A | * | 3/2023 | ............. A61B 34/37 |

* cited by examiner

*Primary Examiner* — Jamil Ahmed

(57) ABSTRACT

A method for detecting a three-dimensional force of a fiber-integrated monolithic clamp guided by metal additive manufacturing, including: pre-preparing a three-dimensional force sensor, including a clamp head, an elastomer, and a transmission component; three groups of etched stepped reduced-diameter fiber gratings are provided on the elastomer; constructing, when the clamp head of the three-dimensional force sensor clamps the tissues, a mechanical model of the elastomer, establishing a relationship between central wavelength drift amounts of the etched stepped reduced-diameter fiber gratings and a temperature as well as the three-dimensional force, and deriving a force and temperature sensitivity matrix; decoupling central wavelength values of the three groups of etched stepped reduced-diameter fiber gratings to measure the three-dimensional force and the temperature; using a long short-term memory neural network to train network parameters; and outputting types of the tissues clamped by the clamp in a classified manner through a random forest algorithm.

9 Claims, 7 Drawing Sheets

Before a force is applied

After a force is applied

METHOD FOR DETECTING THREE-DIMENSIONAL FORCE OF A FIBER-INTEGRATED MONOLITHIC CLAMP GUIDED BY METAL ADDITIVE MANUFACTURING

CROSS-REFERENCE TO RELATED APPLICATIONS

The application claims priority to Chinese patent application 2024114285715, filed on Oct. 14, 2024, the entire contents of which are incorporated herein by reference.

TECHNICAL FIELD

The present disclosure relates to the technical field of optical fiber sensing, in particular relates to a method for detecting a three-dimensional force of a fiber-integrated monolithic clamp guided by metal additive manufacturing.

BACKGROUND

In a process of robot-assisted minimally invasive surgery, due to the limitation of a size of an incision, a vision of a surgeon is restricted. At the same time, the surgeon loses a tactile feeling of tissues of a patient, and is unable to assess characteristics of the tissues of the patient, leading to a variety of problems such as an excessive force causing injuries to the tissues of the patient, affecting a natural course of the surgery, as well as intraoperative and postoperative complications. Existing force sensors are mostly electrical sensors, which are relatively mature in their development, but have shortcomings such as limited sensitivity, electromagnetic interference and cross interference, and poor environmental adaptability.

In recent years, an additive manufacturing technology has shown great potential in processing and manufacturing of optical fiber sensors. Main advantages of this technology are that it can realize manufacturing of a complex structures and seamlessly transform between a plurality of materials. With this technology, it is possible to integrate an elastomer with a sensitive element to manufacture a more miniaturized sensor.

Therefore, based on the above situation, it is highly necessary to provide a method for detecting a three-dimensional force of a fiber-integrated monolithic clamp guided by metal additive manufacturing that is smaller in size, flexible in operation, and performs decoupling and a fault-tolerant measurement on the three-dimensional force and a temperature simultaneously, to reduce accidental injuries and reduce surgical pain and complications.

SUMMARY

In view of this, the present disclosure proposes a method for detecting a three-dimensional force of a fiber-integrated monolithic clamp guided by metal additive manufacturing with a certain a certain fault-tolerant ability for simultaneous measurements of the three-dimensional force and a temperature at a clamp end in a surgical process.

The present disclosure provides a method for detecting a three-dimensional force of a fiber-integrated monolithic clamp guided by metal additive manufacturing, including the following steps:

S1: pre-preparing a three-dimensional force sensor, wherein the three-dimensional force sensor includes a clamp head, an elastomer, and a transmission component, one end of the elastomer in an axial direction is connected with the clamp head, and the clamp head is configured to clamp tissues; another end of the elastomer in the axial direction is provided with the transmission component, and the transmission component passes through the elastomer to be in a transmission connection with the clamp head; and three groups of etched stepped reduced-diameter fiber gratings are provided on the elastomer in a centrosymmetric distribution;

S2: constructing, when the clamp head of the three-dimensional force sensor clamps the tissues, a mechanical model of the elastomer, obtaining a strain of the elastomer under action of the three-dimensional force, establishing, in combination with temperature sensitivity coefficients of the three groups of etched stepped reduced-diameter fiber gratings, a relationship between central wavelength drift amounts of the etched stepped reduced-diameter fiber gratings and a temperature as well as the three-dimensional force, and deriving a force and temperature sensitivity matrix;

S3: decoupling, by solving a generalized inverse matrix of the force and temperature sensitivity matrix as a calibration matrix, central wavelength values of the three groups of etched stepped reduced-diameter fiber gratings to measure the three-dimensional force and the temperature;

S4: filtering three-dimensional force time series data, constructing a training sample, and using a long short-term memory (LSTM) neural network to train network parameters; and predicting three-dimensional force data at a current moment and recovering subsequent interaction force measurement data after training is completed, according to a sample corresponding to current input three-dimensional force data and in combination with historical fault-free three-dimensional force data and fault-free three-dimensional force data prior to the current moment, and realizing a fault-tolerant output of three-dimensional force decoupling under a fault of the etched stepped reduced-diameter fiber gratings; and S5: outputting types of the tissues clamped by the clamp in a classified manner through a random forest algorithm in combination with central wavelength drift amount information of the three groups of etched stepped reduced-diameter fiber gratings.

Based on the above technical solution, preferably, the elastomer includes a hollow double-layer cylinder, two diaphragms, and a plurality of curved connection portions; an inner cylinder is coaxially provided at an inner center of an outer cylinder of the double-layer cylinder, and two axially extending end portions of the inner cylinder are fixedly connected with two axially extending end portions of the outer cylinder respectively; an axially penetrating first through hole is provided at centers of the end portions of the outer cylinder, and the first through hole communicates with an interior of the inner cylinder; a plurality of penetrating second through holes are formed on an end face located between an inner surface of the outer cylinder and an outer surface of the inner cylinder, and the second through holes extend in an axial direction of the outer cylinder and are provided in a penetrating manner; the plurality of second through holes are provided in centrosymmetry with respect to the first through hole;

the two diaphragms are provided in a spaced manner on outer sides of the axially extending end portions of the outer cylinder and spaced apart from the outer cylinder, a center of each of the two diaphragms is provided with a penetrating third through hole, edges of the two diaphragms are further provided with a plurality of optical fiber fixing holes, and the optical fiber fixing holes are provided in a penetrating manner in the axial direction of the outer cylinder on the one hand, and further extend outward in radial directions of the diaphragms on the other hand; the third through holes and the first through hole communicate with each other; the plurality of second through holes and the plurality of optical fiber fixing holes are provided in a one-to-one correspondence and mutual communication; and diameters of the two diaphragms are approximately equal a diameter of the outer cylinder;

the plurality of curved connection portions are provided between the two diaphragms and end faces of the outer cylinder, the curved connection portions are fixedly connected with the two diaphragms and the outer cylinder respectively, one ends of the curved connection portions close to the outer cylinder are tangent to contours of the second through holes, and one ends of the curved connection portions away from the outer cylinder are flush with edges of the optical fiber fixing holes; inner surfaces of the plurality of curved connection portions are located on the same virtual cylinder, the virtual cylinder and the inner cylinder are coaxially provided, and a diameter of the virtual cylinder is larger than that of the first through hole, and the diameter of the virtual cylinder is smaller than an inner diameter of the outer cylinder;

the transmission component passes through the first through hole and the third through holes sequentially and is in a transmission connection with the clamp head; and the three groups of etched stepped reduced-diameter fiber gratings pass through the optical fiber fixing holes and the second through holes, and parts of the step reducing fiber gratings between the two diaphragms are in a suspended-tensioned state, and a length of suspended and tensioned sections of the step reducing fiber gratings is the same as an axial length of the outer cylinder.

Preferably, the three groups of etched stepped reduced-diameter fiber gratings each include a metallized optical fiber, the metallized optical fiber is provided with a grating region, and the grating region includes a normal section and a etched stepped reduced-diameter section provided sequentially; and metal nickel-plated layers are provided in a spaced manner at two ends of the grating region in an axially extending direction, and the metal nickel-plated layer is fixedly connected with an inner surface of the optical fiber fixing hole.

Further preferably, a method for preparing the elastomer is: processing the outer cylinder, the inner cylinder, the two diaphragms, and the plurality of curved connection portions through a method of additive manufacturing of printing a titanium alloy powder, reserving a half of each of the second through holes and the optical fiber fixing holes, afterwards, placing the etched stepped reduced-diameter fiber grating in the correspondingly provided half of the second through hole and optical fiber fixing hole, next preparing the complete second through hole and optical fiber fixing hole by laser scanning printing of the titanium alloy powder to fix the etched stepped reduced-diameter fiber grating, and then providing the three groups of etched stepped reduced-diameter fiber gratings and the transmission component on the elastomer sequentially in a penetrating manner.

Further preferably, step S2 is specified as:

the three-dimensional force sensor is affected by an axial force Fz, a transverse force $F_X$, a longitudinal force $F_y$, and the temperature;

when the three-dimensional force sensor is only subjected to action of the axial force Fz, strains of the suspended-tensioned sections of the three groups of etched stepped reduced-diameter fiber gratings are: $\varepsilon_{Fz1}=\varepsilon_{Fz2}=\varepsilon_{Fz3}=\varepsilon_{Fz}$; then when the elastomer is only subjected to the action of the axial force Fz, wavelength drifts corresponding to the normal sections and the etched stepped reduced-diameter sections of the three groups of etched stepped reduced-diameter fiber gratings are:

$$
\begin{cases}
\Delta\lambda_{1-n} = \dfrac{C}{1+C}\lambda_{1-n}(1-P_e)\varepsilon_{Fz} = K_{z1-n} \\[2mm]
\Delta\lambda_{1-e} = \dfrac{1}{1+C}\lambda_{1-e}(1-P_e)\varepsilon_{Fz} = K_{z1-e} \\[2mm]
\Delta\lambda_{2-n} = \dfrac{C}{1+C}\lambda_{2-n}(1-P_e)\varepsilon_{Fz} = K_{z2-n} \\[2mm]
\Delta\lambda_{2-e} = \dfrac{1}{1+C}\lambda_{2-e}(1-P_e)\varepsilon_{Fz} = K_{z2-e} \\[2mm]
\Delta\lambda_{3-n} = \dfrac{C}{1+C}\lambda_{3-n}(1-P_e)\varepsilon_{Fz} = K_{z3-n} \\[2mm]
\Delta\lambda_{3-e} = \dfrac{1}{1+C}\lambda_{3-e}(1-P_e)\varepsilon_{Fz} = K_{z3-e}
\end{cases},
$$

where $\Delta\lambda_{i-n}$ and $\Delta\lambda_{i-e}$ are wavelength drift amounts of central wavelengths generated by the normal section and the etched stepped reduced-diameter section of the suspended-tensioned etched stepped reduced-diameter fiber grating respectively, $\lambda_{i-n}$ and $\lambda_{i-e}$ are initial central wavelengths of the normal section and the etched stepped reduced-diameter section of the suspended-tensioned etched stepped reduced-diameter fiber grating respectively, and i=1,2,3; C is a strain sensitivity ratio of the normal section and the etched stepped reduced-diameter section of the etched stepped reduced-diameter fiber grating; $K_{zi-n}$ and $K_{zi-e}$ are force sensitivities of the normal section and the etched stepped reduced-diameter section of the etched stepped reduced-diameter fiber grating when the elastomer is only subjected to the action of the axial force Fz; and $P_e$ is an effective elastic-optic constant of a fiber core of the optical fiber;

when the three-dimensional force sensor is only subjected to action of the transverse force $F_X$, the elastomer undergoes a transverse deformation, the three groups of etched stepped reduced-diameter fiber gratings are named a first etched stepped reduced-diameter fiber grating, a second etched stepped reduced-diameter fiber grating, and a third etched stepped reduced-diameter fiber grating respectively; the first etched stepped reduced-diameter fiber grating undergoes a deformation in a direction opposite to the second etched stepped reduced-diameter fiber grating, and the deformation of the second etched stepped reduced-diameter fiber grating is a half of the deformation of the first etched stepped reduced-diameter fiber grating; the second etched stepped reduced-diameter fiber grating undergoes a deformation of an equal magnitude and the same direction as that of the third etched stepped reduced-diameter fiber grating, $$
\varepsilon_{Fx2} = \varepsilon_{Fx3} = -\frac{\varepsilon_{Fx1}}{2}
$$

is met, where $\varepsilon_{Fx1}$ is the deformation that occurs to the first etched stepped reduced-diameter fiber grating, $\varepsilon_{Fx2}$ is the deformation that occurs to the second etched stepped reduced-diameter fiber grating, and $\varepsilon_{Fx3}$ is the deformation that occurs to the third etched stepped reduced-diameter fiber grating; thus, when the elastomer is only subjected to the action of the transverse force $F_X$, wavelength drifts corresponding to the normal sections and the etched stepped reduced-diameter sections of the three groups of etched stepped reduced-diameter fiber gratings are:

$$
\begin{cases}
\Delta\lambda_{1-n} = \dfrac{C}{1+C}\lambda_{1-n}(1 - P_e)\varepsilon_{Fx1} = K_{x1-n} \\[2mm]
\Delta\lambda_{1-e} = \dfrac{1}{1+C}\lambda_{1-e}(1 - P_e)\varepsilon_{Fx1} = K_{x1-e} \\[2mm]
\Delta\lambda_{2-n} = \dfrac{C}{(1+C)}\lambda_{2-n}(1 - P_e)\varepsilon_{Fx2} = K_{x2-n} \\[2mm]
\Delta\lambda_{2-e} = \dfrac{1}{(1+C)}\lambda_{2-e}(1 - P_e)\varepsilon_{Fx2} = K_{x2-e} \\[2mm]
\Delta\lambda_{3-n} = \dfrac{C}{(1+C)}\lambda_{3-n}(1 - P_e)\varepsilon_{Fx3} = K_{x3-n} \\[2mm]
\Delta\lambda_{3-e} = \dfrac{1}{(1+C)}\lambda_{3-e}(1 - P_e)\varepsilon_{Fx3} = K_{x3-e}
\end{cases},
$$

where $K_{xi-n}$ and $K_{xi-e}$ are force sensitivities of the normal section and the etched stepped reduced-diameter section of the etched stepped reduced-diameter fiber grating when the elastomer is only subjected to the action of the transverse force $F_X$;

when the three-dimensional force sensor is only subjected to action of the longitudinal force $F_y$, the elastomer undergoes a longitudinal deformation, the first etched stepped reduced-diameter fiber grating is located on a neutral layer, the second etched stepped reduced-diameter fiber grating undergoes a deformation of an equal magnitude and an opposite direction to the third etched stepped reduced-diameter fiber grating, such that deformations of the second etched stepped reduced-diameter fiber grating and the third etched stepped reduced-diameter fiber grating are $\varepsilon_{Fy2}$ and $\varepsilon_{Fy3}$ when the longitudinal force $F_y$ acts, then when the elastomer is only subjected to the action of the longitudinal force $F_y$, wavelength drifts corresponding to the normal sections and the etched stepped reduced-diameter sections of the three groups of etched stepped reduced-diameter fiber gratings are:

$$
\begin{cases}
\Delta\lambda_{1-n} = 0 \\[2mm]
\Delta\lambda_{1-e} = 0 \\[2mm]
\Delta\lambda_{2-n} = \dfrac{C}{(1+C)}\lambda_{2-n}(1 - P_e)\varepsilon_{Fy2} = K_{y2-n} \\[2mm]
\Delta\lambda_{2-e} = \dfrac{1}{(1+C)}\lambda_{2-e}(1 - P_e)\varepsilon_{Fy2} = K_{y2-e} \\[2mm]
\Delta\lambda_{3-n} = \dfrac{C}{(1+C)}\lambda_{3-n}(1 - P_e)\varepsilon_{Fy3} = K_{y3-n} \\[2mm]
\Delta\lambda_{3-e} = \dfrac{1}{(1+C)}\lambda_{3-e}(1 - P_e)\varepsilon_{Fx3} = K_{y3-e}
\end{cases},
$$

where $K_{yi-n}$ and $K_{yi-e}$ are force sensitivities of the normal section and the etched stepped reduced-diameter section of the etched stepped reduced-diameter fiber grating when the elastomer is only subjected to the action of the longitudinal force $F_y$;

When an ambient temperature changes, the central wavelength of the optical fiber drifts due to a thermo-optic effect of the optical fiber, a thermal expansion effect, and an elastic-optic effect caused by an internal thermal stress. Wavelength drifts corresponding to the normal sections and the etched stepped reduced-diameter sections of the three groups of etched stepped reduced-diameter fiber gratings under an influence of the temperature are:

$$
\begin{cases}
\Delta\lambda_{t1-n} = C_T\lambda_{1-n}\Delta T = K_{T1-n} \\[1mm]
\Delta\lambda_{t1-e} = C_T\lambda_{1-e}\Delta T = K_{T1-e} \\[1mm]
\Delta\lambda_{t2-n} = C_T\lambda_{2-n}\Delta T = K_{T2-n} \\[1mm]
\Delta\lambda_{t2-e} = C_T\lambda_{2-e}\Delta T = K_{T2-e} \\[1mm]
\Delta\lambda_{t3-n} = C_T\lambda_{3-n}\Delta T = K_{T3-n} \\[1mm]
\Delta\lambda_{t3-e} = C_T\lambda_{3-e}\Delta T = K_{T3-e}
\end{cases},
$$

where $\Delta\lambda_{ti-n}$ and $\Delta\lambda_{ti-e}$ are the wavelength drifts of the normal sections and the etched stepped reduced-diameter sections of the three groups of etched stepped reduced-diameter fiber gratings under action of the temperature; a relative temperature sensitivity coefficient of the etched stepped reduced-diameter fiber grating is $C_T = \zeta + \sigma$, $\zeta$ is a thermo-optic coefficient of the etched stepped reduced-diameter fiber grating, $\sigma$ is a linear thermal expansion coefficient of the etched stepped reduced-diameter fiber grating; $K_{Ti-n}$ and $K_{Ti-e}$ are temperature sensitivities of the normal section and the etched stepped reduced-diameter section of each etched stepped reduced-diameter fiber grating respectively when the elastomer is only subjected to the influence of the temperature.

Synthesizing the above cases where the force and the temperature act separately, a relationship matrix of the central wavelength drift amounts of reflectance spectra of the three groups of etched stepped reduced-diameter fiber gratings and the three-dimensional force as well as the temperature is obtained as:

$$
\begin{bmatrix}
\Delta\lambda_{1-n} \\
\Delta\lambda_{1-e} \\
\Delta\lambda_{2-n} \\
\Delta\lambda_{2-e} \\
\Delta\lambda_{3-n} \\
\Delta\lambda_{3-e}
\end{bmatrix}
= \Delta\lambda_{6\times1} = K_{6\times4} =
\begin{bmatrix}
K_{x1-n} & 0 & K_{z1-n} & K_{T1-n} \\
K_{x1-e} & 0 & K_{z1-e} & K_{T1-e} \\
K_{x2-n} & K_{y2-n} & K_{z2-n} & K_{T2-n} \\
K_{x2-e} & K_{y2-e} & K_{z2-e} & K_{T2-e} \\
K_{x3-n} & K_{y3-n} & K_{z3-n} & K_{T3-n} \\
K_{x3-e} & K_{y3-e} & K_{z3-e} & K_{T3-e}
\end{bmatrix}
\begin{bmatrix}
F_x \\
F_y \\
F_z \\
\Delta T
\end{bmatrix},
$$

where $\Delta\lambda_{6\times1}$ is a central wavelength drift amount of the normal section and the etched stepped reduced-diameter section of each etched stepped reduced-diameter fiber grating, and $K_{6\times4}$ is a force and temperature sensitivity matrix.

Further preferably, a content of step S3 is: solving the three-dimensional force and the temperature $$
\begin{bmatrix}
F_x \\
F_y \\
F_z \\
\Delta T
\end{bmatrix}
= C_{4\times6} \cdot \Delta\lambda_{6\times1}
$$

by solving the generalized inverse matrix $C_{4\times6}$ of the sensitivity matrix $K_{6\times4}$ as the calibration matrix, and through the central wavelength drift amount $\Delta\lambda_{6\times1}$ of the normal section and the etched stepped reduced-diameter section of each etched stepped reduced-diameter fiber grating.

Yet further preferably, a content of step S4 is: using a Kalman filtering method to filter the historically measured three-dimensional force time series data of the three-dimensional force sensor, and normalizing the filtered three-dimensional force time series data; dividing the normalized three-dimensional force time series data into a training set and a test set, wherein the training set is used to establish a model, and the test set is used to verify a generalization ability of the model; and using a sliding time window to construct the training sample, building an LSTM neural network model, and using the training set to train parameters of the LSTM neural network model.

Further preferably, the content of step S5 is: using the random forest algorithm to classify the tissues clamped by the clamp head, using the three-dimensional force obtained from a decoupling calculation as an input set of the random forest algorithm, using the types of the tissues as outputs, setting, in a training process of the random forest algorithm, the number of decision trees to be 100, a minimum number of leaves to be 1, and the number of candidate features for feature selection for each tree to be 2, using 70% of the input set as the training set, and using remaining 30% of the input set as the test set to verify the trained random forest algorithm.

Further preferably, a diameter of the etched stepped reduced-diameter fiber grating is 125 μm, a length of the grating region is 3 mm, and the normal section and the etched stepped reduced-diameter section each contain a half of the grating region.

Compared with the prior art, the method for detecting the three-dimensional force of a fiber-integrated monolithic clamp guided by metal additive manufacturing provided by the present disclosure has the following beneficial effects:

(1) Measurement of the three-dimensional force and the temperature is realized by a provided elastomer sensing module. The use of the reducing fiber gratings as sensing elements makes an overall structure of the sensor more compact, can exclude the influence of temperature changes on measurement accuracy, and has a good anti-electromagnetic interference performance. Through a self-enclosed structural design, the titanium alloy clastic metal material that has both biocompatibility and corrosion resistance, as well as an encapsulation manner combined with an additive manufacturing process, the sensor has excellent adaptability in a tissue fluid erosion environment and a high temperature sterilization environment.

(2) Through a structural design of the double-layer diaphragms, the introduction of the reducing-section fiber gratings and pre-tensioning of the fiber gratings, it is arranged in a suspended manner, and thus the sensor obtains a very high sensitivity, so that the elastomer and a force sensing module composed of the three groups of etched stepped reduced-diameter fiber gratings are more sensitive to changes in temperature and three-dimensional force simultaneously.

(3) Integrated manufacturing and encapsulation of the clamp end, the elastomer, the integrated end, the flexible metal tube, and the metallized reducing optical fibers of the sensor is realized by introducing the metal additive technology. Embedding the etched stepped reduced-diameter fiber gratings directly in the process of 3D printing may reduce the creep and improve the stability and accuracy of the elastomer and the etched stepped reduced-diameter fiber gratings as a whole. Through in-situ measurement of a wrist force of the clamp, a transfer path of the force may be reduced, the perturbation of embedding of the optical fibers may be reduced, and the accuracy and stability of the sensor may be improved.

(4) The etched stepped reduced-diameter fiber gratings may provide the sensor with abundant multi-channel central wavelength data, give the sensor a fault-tolerant measurement ability in combination with the long and short-term memory neural network algorithm, and further improve the reliability of the sensor. Even if one or two etched stepped reduced-diameter fiber gratings fail, the sensor may continue to be used reliably. By introducing the random forest algorithm to classify and predict the tissues with different mechanical performances in the clamping process, the sensor has a wider range of application scenarios.

BRIEF DESCRIPTION OF DRAWINGS

To describe the technical solutions in the embodiments of the present invention or in the related art more clearly, the following briefly introduces the accompanying drawings for describing the embodiments or the related art. Apparently, the accompanying drawings in the following description show merely some embodiments of the present invention, and a person of ordinary skill in the art may still derive other drawings from the accompanying drawings without creative efforts.

Figure 1:
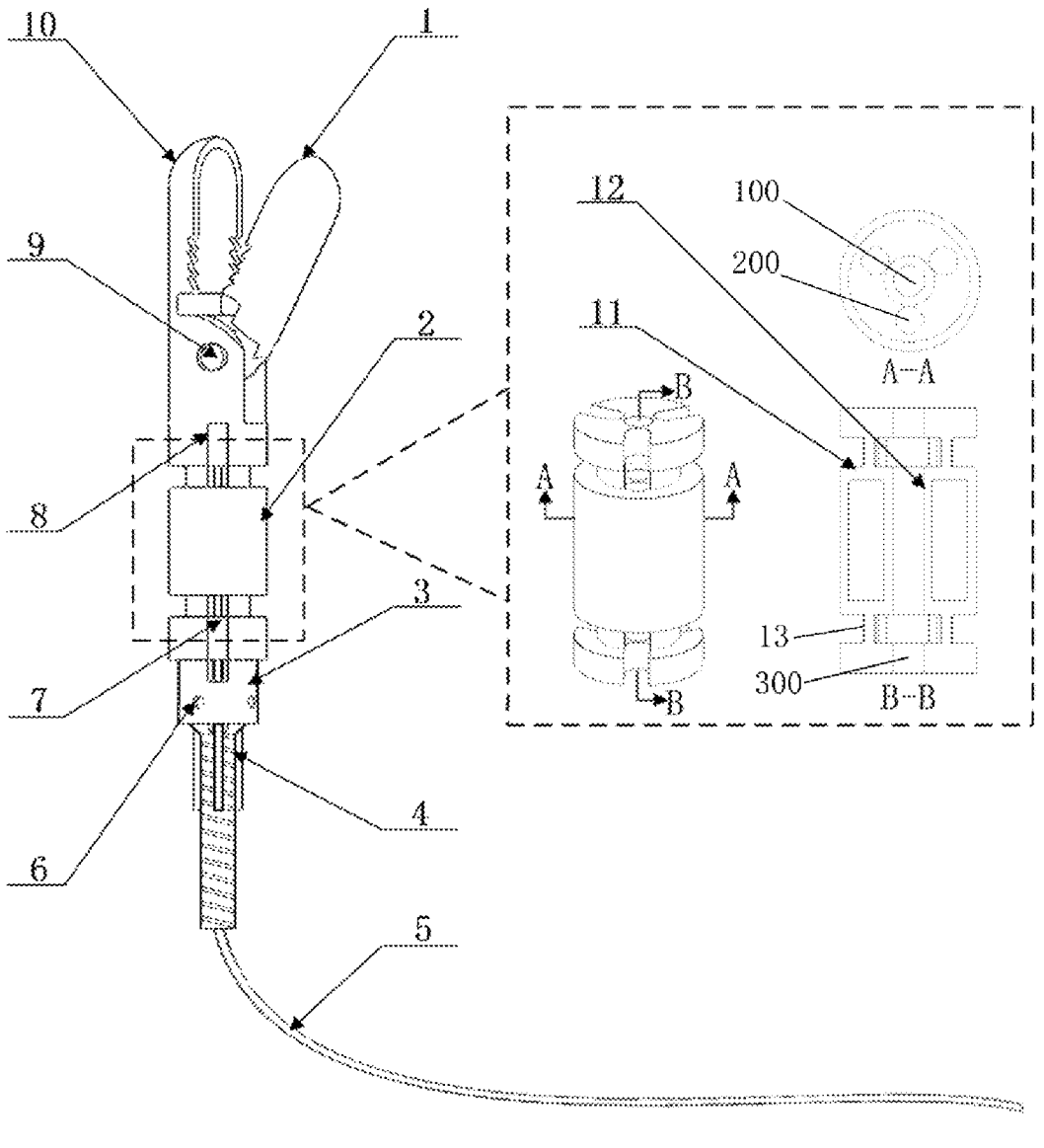
FIG. 1 is a three-dimensional diagram of a three-dimensional force sensor and a clamp as a whole for a method for detecting a three-dimensional force of a fiber-integrated monolithic clamp guided by metal additive manufacturing of the present disclosure.

Reference numerals: 1, clamp head; 2, elastomer; 3, integrated end; 4, flexible metal tube; 5, nickel-titanium alloy wire; 6, pin hole; 7, etched stepped reduced-diameter fiber grating; 8, optical fiber fixing hole; 9, pin fixing hole; 10, clamp end; 11, diaphragm; 12, double-layer cylinder; 13, curved connection portion; 101, metal nickel-plated layer; 102—normal section; 103—etched stepped reduced-diameter section; 104—first etched stepped reduced-diameter fiber grating, 105—second etched stepped reduced-diameter fiber grating; 106—third etched stepped reduced-diameter fiber grating, 107—male-female pin, 108—drive wire connector, 109—pin; 100, first through hole; 200, second through hole; and 300, third through hole.

DETAILED DESCRIPTION OF THE EMBODIMENTS

The technical solutions in the embodiments of the present invention will be clearly and completely described below with reference to the embodiments of the present invention, and it is obvious that the described embodiments are only a part of the embodiments of the present invention but not all of them. All other embodiments obtained by a person of ordinary skill in the art based on the embodiments of present disclosure without making creative efforts shall fall within the protection scope of present disclosure.

Figure 2:
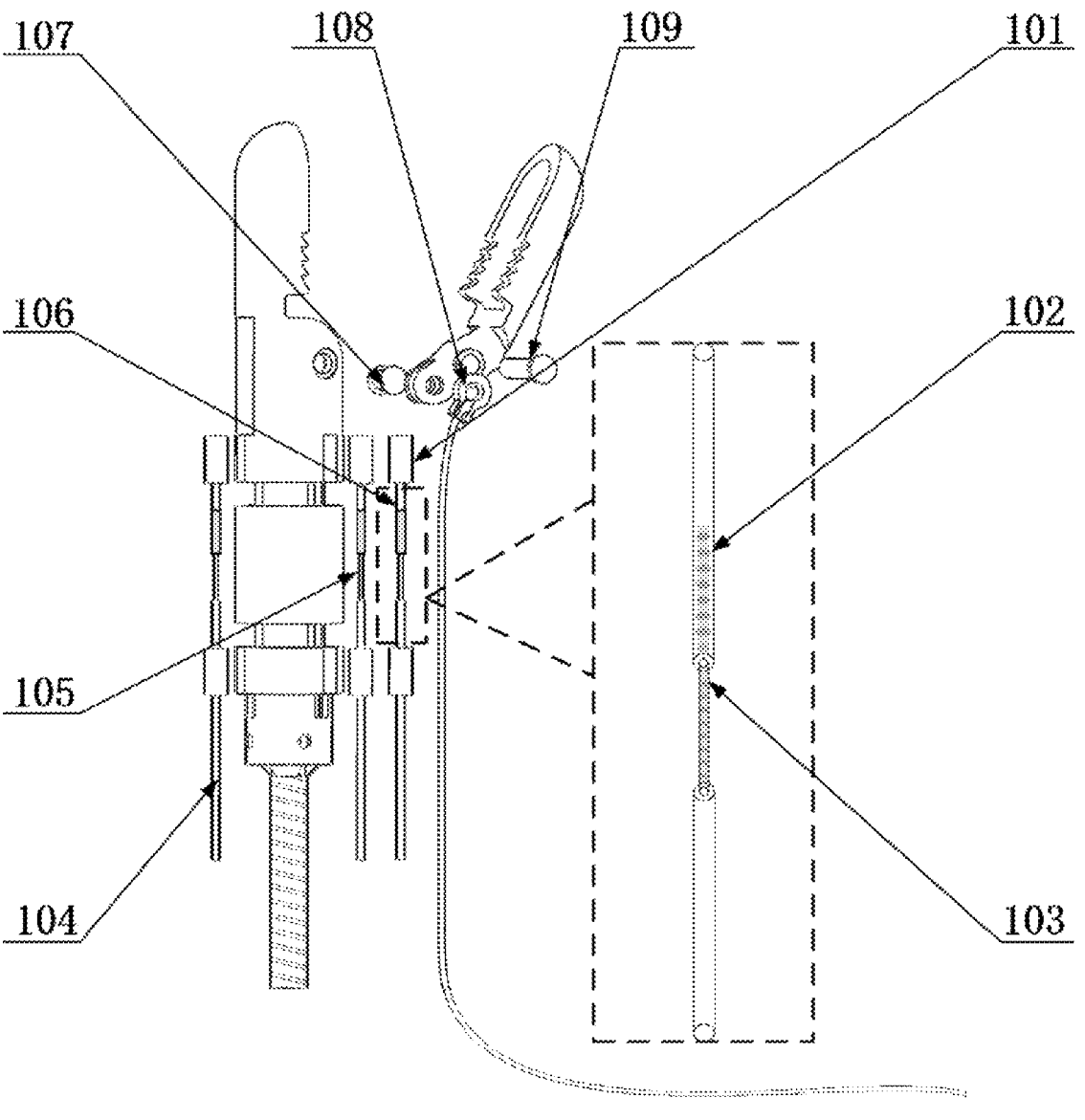
FIG. 2 is a three-dimensional diagram of an exploded state of FIG. 1.

As shown in FIG. 1 and FIG. 2, the present disclosure provides a method for detecting a three-dimensional force of a fiber-integrated monolithic clamp guided by metal additive manufacturing, including the following steps:

S1: a three-dimensional force sensor is pre-prepared. The three-dimensional force sensor includes a clamp head 1, an elastomer 2, and a transmission component. One end of the elastomer 2 in an axial direction is connected with the clamp head 1. The clamp head 1 is configured to clamp tissues. Another end of the elastomer 2 in the axial direction is provided with the transmission component. The transmission component passes through the elastomer 2 to be in a transmission connection with the clamp head 1. Three groups of etched stepped reduced-diameter fiber gratings 7 are provided on the elastomer 2 in a centrosymmetric distribution.

A dashed box in FIG. 1 shows a partially enlarged stereogram, a sectional view in an A-A direction, and a sectional view in a B-B direction of the elastomer 2. One end of the elastomer 2 has an outward extending clamp end 10. The clamp end is configured to be connected with the clamp head 1. The transmission component includes a flexible metal tube 4, a nickel-titanium alloy wire 5, pin fixing holes 9, a drive wire connector 108, and a pin 109. Another end of the elastomer 2 has an outward extending integrated end 3 for assembling the transmission component. The integrated end 3 is provided with the flexible metal tube 4 and the nickel-titanium alloy wire 5. The clamp head 1 is of a single-opening design. The two different pin fixing holes 9 and the drive wire connector 108 are configured in the clamp head 1. Reliability of a structure is improved by using a laser welding technology to fix the pin to the clamp end 10. A nickel-titanium alloy wire fixing hole is provided at a tail end of the drive wire connector 108. The nickel-titanium alloy wire 5 passes through the flexible metal tube 4 and the elastomer 2 sequentially, and one end being an embedded end portion is embedded in the nickel-titanium alloy wire fixing hole, which improves structural strength and simplifies an installation process. A main part of the transmission component of the three-dimensional force sensor may be installed only by matching two male-female pins 107 and the pin 109 with a pin hole 6. A movable part of the clamp head is pivotally connected to a fixed part through a pin, and is further fixed to the nickel-titanium alloy wire 5 through a pin, thereby realizing opening and closing clamping functions of the clamp head.

Figure 3:
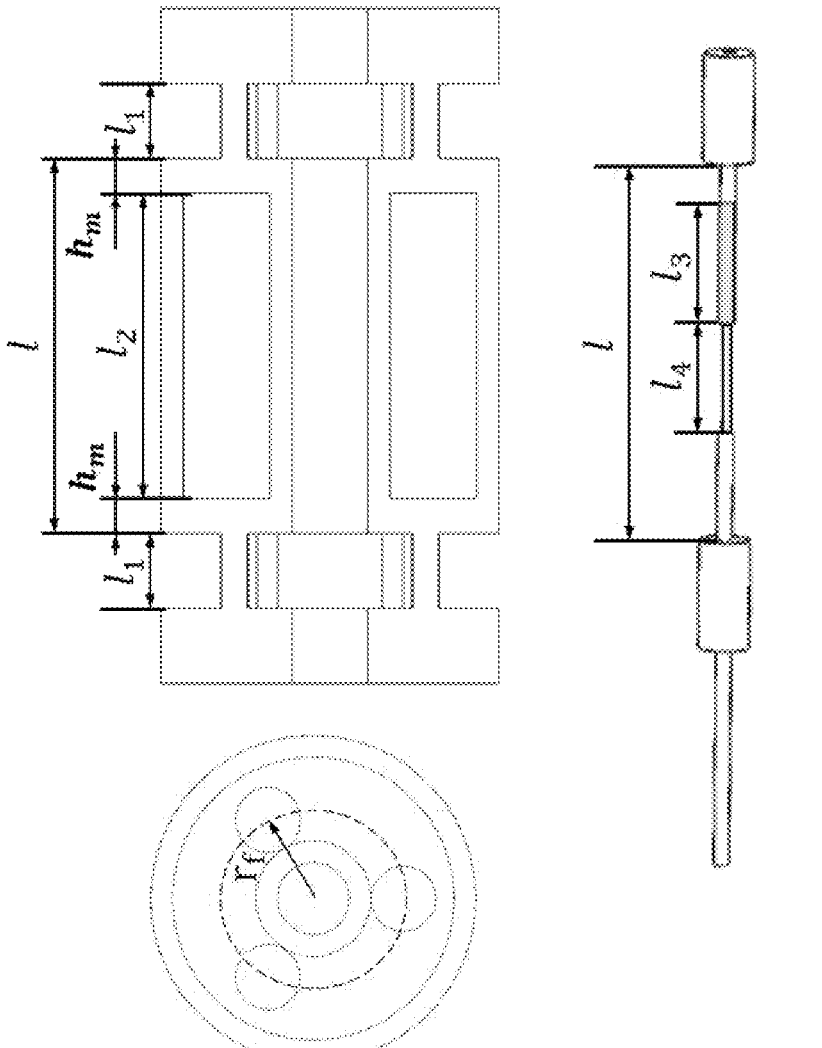
FIG. 3 is a schematic diagram of an elastomer and a etched stepped reduced-diameter fiber grating for a method for detecting a three-dimensional force of a fiber-integrated monolithic clamp guided by metal additive manufacturing of the present disclosure.

As shown in FIG. 1 in combination with FIG. 2 and FIG. 3, the A-A sectional view and the B-B sectional view of FIG. 1 show that the elastomer 2 includes a hollow double-layer cylinder 12, two diaphragms 11, and a plurality of curved connection portions 13. An inner cylinder is coaxially provided at an inner center of an outer cylinder of the double-layer cylinder 12. Two axially extending end portions of the inner cylinder are fixedly connected with two axially extending end portions of the outer cylinder respectively. An axially penetrating first through hole 100 is provided at centers of the end portions of the outer cylinder. The first through hole 100 communicates with an interior of the inner cylinder. A plurality of penetrating second through holes 200 are formed on an end face located between an inner surface of the outer cylinder and an outer surface of the inner cylinder. The second through holes 200 extend in an axial direction of the outer cylinder and are provided in a penetrating manner. The plurality of second through holes 200 are provided in centrosymmetry with respect to the first through hole 100.

The two diaphragms 11 are provided in a spaced manner on outer sides of the axially extending end portions of the outer cylinder and spaced apart from the outer cylinder. A center of each of the two diaphragms 11 is provided with a penetrating third through hole 300. Edges of the two diaphragms 11 are further provided with a plurality of optical fiber fixing holes 8. The optical fiber fixing holes 8 are provided in a penetrating manner in the axial direction of the outer cylinder on the one hand, and further extend outward in a radial direction of the diaphragms 11 on the other hand. The third through holes 300 and the first through hole 100 communicate with each other. The plurality of second through holes 200 and the plurality of optical fiber fixing holes 8 are provided in a one-to-one correspondence and mutual communication. Diameters of the two diaphragms 11 are approximately equal a diameter of the outer cylinder. A structure of the double-layer cylinder 12 may be used to communicate the nickel-titanium alloy wire and protect optical fibers from erosion by tissue fluids. A structure of the two diaphragms 11 may improve axial force sensitivity of the three-dimensional force sensor.

The plurality of curved connection portions 13 are provided between the two diaphragms 11 and end faces of the outer cylinder. The curved connection portions 13 are fixedly connected with the two diaphragms 11 and the outer cylinder respectively. One ends of the curved connection portions 13 close to the outer cylinder are tangent to contours of the second through holes 200. One ends of the curved connection portions 13 away from the outer cylinder are flush with edges of the optical fiber fixing holes 8. Inner surfaces of the plurality of curved connection portions 13 are located on the same virtual cylinder. The virtual cylinder and the inner cylinder are coaxially provided, and a diameter of the virtual cylinder is larger than that of the first through hole 100. The diameter of the virtual cylinder is smaller than an inner diameter of the outer cylinder. In a schematic diagram at a lower part of FIG. 3, central axes of the respective second through holes 200 are also distributed on one dashed circle. $r_f$ is a radius of the dashed circle, i.e., a distance from the first through hole 100 to the second through holes 200.

The transmission component passes through the first through hole 100 and the third through holes 300 sequentially and is in a transmission connection with the clamp head 1. The three groups of etched stepped reduced-diameter fiber gratings 7 pass through the optical fiber fixing holes 8 and the second through holes 200, and parts of the step reducing fiber gratings between the two diaphragms 11 are in a suspended-tensioned state. A length of suspended-tensioned sections of the step reducing fiber gratings is the same as an axial length of the outer cylinder.

The three groups of etched stepped reduced-diameter fiber gratings 7 each include a metallized optical fiber. The metallized optical fiber is provided with a grating region.

The grating region includes a normal section 102 and a etched stepped reduced-diameter section 103 provided sequentially. Metal nickel-plated layers 101 are provided in a spaced manner at two ends of the grating region in an axially extending direction. The metal nickel-plated layer 101 is fixedly connected with an inner surface of the optical fiber fixing hole 8. A fixed part of the etched stepped reduced-diameter fiber grating 7 to the elastomer 2 is metalized with the metal nickel-plated layer 101 to protect the fiber grating, so that the fiber grating can be embedded in the elastomer 2 in a tensioned-suspended manner. The normal section of the etched stepped reduced-diameter fiber grating 7 is represented by 102, and the etched stepped reduced-diameter section is represented by 103. The three groups of etched stepped reduced-diameter fiber gratings 7 are named a first etched stepped reduced-diameter fiber grating 104, a second etched stepped reduced-diameter fiber grating 105, and a third etched stepped reduced-diameter fiber grating 106 respectively.

As a preferred implementation, a diameter of the etched stepped reduced-diameter fiber grating 7 is 125 μm, a length of the grating region is 3 mm, and the normal section and the etched stepped reduced-diameter section each contain a half of the grating region. The first etched stepped reduced-diameter fiber grating 104, the second etched stepped reduced-diameter fiber grating 105, and the third etched stepped reduced-diameter fiber grating 106 are all circumferentially and uniformly distributed parallel to a central axis of the elastomer. An included angle between central axes of the adjacent etched stepped reduced-diameter fiber gratings is 120°, which may prevent the optical fibers from chirping, improve a mechanical performance of the three-dimensional force sensor, and meanwhile reduce a repeatability error of the three-dimensional force sensor.

Figure 4:
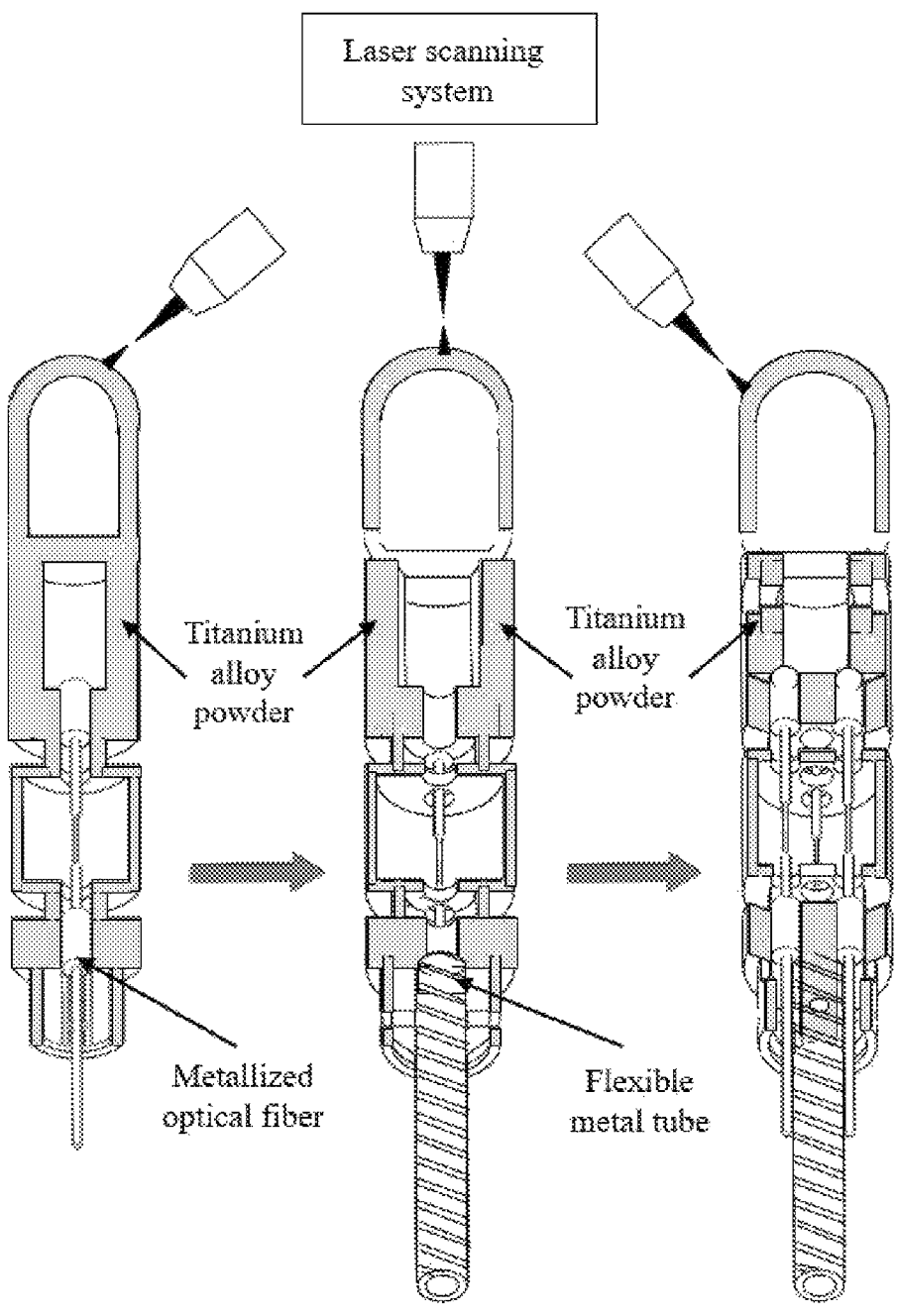
FIG. 4 is a schematic diagram of an additive manufacturing process for a method for detecting a three-dimensional force of a fiber-integrated monolithic clamp guided by metal additive manufacturing of the present disclosure.
Figure 5:
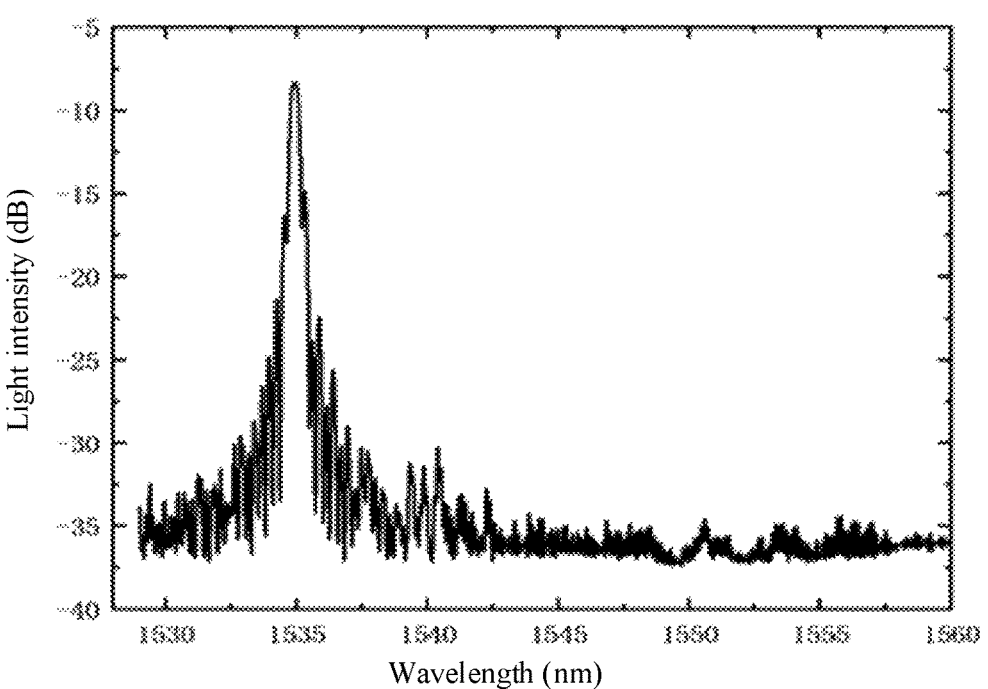
FIG. 5 is a spectral diagram of a etched stepped reduced-diameter fiber grating embedded in an elastomer before and after a force is applied for a method for detecting a three-dimensional force of a fiber-integrated monolithic clamp guided by metal additive manufacturing of the present disclosure.
Figure 5:
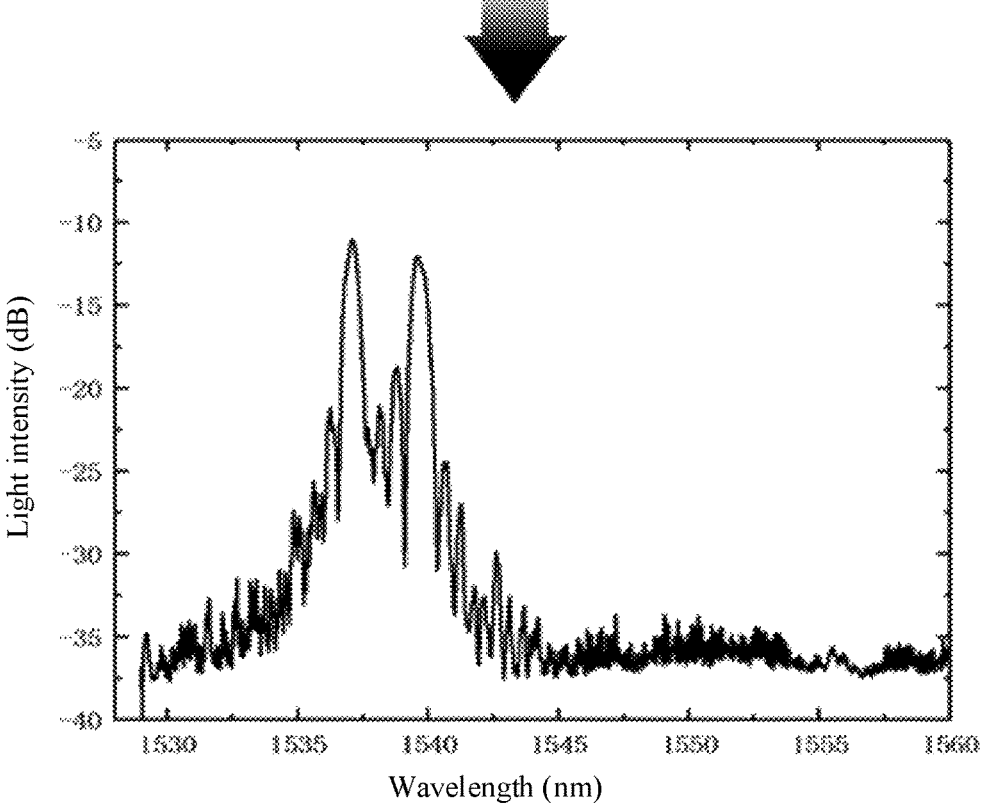

Referring to FIG. 4, a method for preparing the elastomer 2 is: processing the outer cylinder, the inner cylinder, the two diaphragms 11, and the plurality of curved connection portions 13 through a method of additive manufacturing of printing a titanium alloy powder, reserving a half of each of the second through holes 200 and the optical fiber fixing holes 8, afterwards, placing the etched stepped reduced-diameter fiber grating 7 in the correspondingly provided half of the second through hole 200 and optical fiber fixing hole 8, next preparing the complete second through hole 200 and optical fiber fixing hole 8 by laser scanning printing of the titanium alloy powder to fix the etched stepped reduced-diameter fiber grating 7, and then providing the three groups of etched stepped reduced-diameter fiber gratings 7 and the transmission component on the elastomer 2 sequentially in a penetrating manner. That is, a bottom-to-top printing manner is used. When printing reaches the first through hole 100, the second through holes, and the third through holes 300, the printing is suspended to allow for placement of the etched stepped reduced-diameter fiber gratings 7 and the nickel-titanium alloy wire 5. In a printing process, a curing process of the metal nickel-plated layers 101 of the etched stepped reduced-diameter fiber gratings 7 and the diaphragms may be completed. The metallized optical fiber marked in FIG. 4 refers to the etched stepped reduced-diameter fiber grating 7 having the metal nickel-plated layer 101. FIG. 5 is a spectral diagram of the etched stepped reduced-diameter fiber grating embedded in the elastomer before and after a force is applied. When the etched stepped reduced-diameter fiber grating embedded in the elastomer is subjected to action of the same external force, central wavelengths of the normal section 102 and the etched stepped reduced-diameter section 103 of the grating region generate two different offsets.

Similarly, the clamp end 10, the clamp head 1, the drive wire connector 108, the elastomer 2, and the integrated end 3 are prepared through an additive manufacturing technology with a titanium alloy as a material, so that the three-dimensional force sensor prepared in this way has good biocompatibility.

S2: when the clamp head 1 of the three-dimensional force sensor clamps the tissues, a mechanical model of the elastomer 2 is constructed, a strain of the elastomer 2 under action of the three-dimensional force is obtained, a relationship between central wavelength drift amounts of the etched stepped reduced-diameter fiber gratings 7 and a temperature as well as the three-dimensional force is established in combination with temperature sensitivity coefficients of the three groups of etched stepped reduced-diameter fiber gratings 7, and a force and temperature sensitivity matrixm is derived.

Step S2 is specified as:

the three-dimensional force sensor is affected by an axial force Fz, a transverse force $F_x$, a longitudinal force $F_y$, and the temperature.

When the force acts, the two sections of the grating region of the etched stepped reduced-diameter fiber grating 7 generate different degrees of strains. It may be seen in combination with mechanics of materials that strain values of the normal section 102 and the etched stepped reduced-diameter section 103 under the action of the force should meet:

$$
\begin{cases}
\varepsilon_{Fi} = \dfrac{\varepsilon_1(l - l_4)}{l} + \dfrac{\varepsilon_2 l_4}{l} \\
\dfrac{\varepsilon_1}{\varepsilon_2} = \dfrac{A_2}{A_1}
\end{cases},
$$

where $\varepsilon_{F_i}$ is a strain generated by an i-th suspended-tensioned etched stepped reduced-diameter fiber grating 7, and $\varepsilon_1$ and $\varepsilon_2$ represent strains of a normal section 102 and a etched stepped reduced-diameter section 103 of the i-th suspended-tensioned etched stepped reduced-diameter fiber grating 7, i=1,2,3.

When the three-dimensional force sensor is only subjected to action of the axial force Fz, the elastomer 2 undergoes an axial deformation. In combination with structural mechanics, a tension and compression deformation of the elastomer 2 is obtained:

$$
\delta_z = \int_0^{l+2l_1} \frac{F_z}{EA} dx =
$$
$$
2\int_0^{l_1} \frac{F_z}{E_1 A_{l1}} dx + 2\int_0^{h_m} \frac{F_z}{E_1 A_m + E_f A_f} dx + \int_0^{l_2} \frac{F_z}{E_1 A_{l2} + E_f A_f} dx,
$$

where l is the axial length of the outer cylinder, $l_1$ is an axial length of the curved connection portion 13, $l_2$ is a thickness of the outer cylinder excluding closed regions of the two end portions, $l_3$ is an axial length of the normal section 102 of the etched stepped reduced-diameter fiber grating 7, $l_4$ is an axial length of the etched stepped reduced-diameter section 103 of the etched stepped reduced-diameter fiber grating 7, $E_1$ and $E_f$ are an modulus of elasticity of the elastomer 2 and a modulus of elasticity of the etched stepped reduced-diameter fiber grating 7 respectively, $A_{l1}$ is a radial sectional area of the curved connection portion 13, $A_{l2}$ is a sectional area of the outer cylinder at a non-end portion position, $A_m$ is a radial sectional area of the diaphragm 11, $A_f$ is a radial sectional area of the etched stepped reduced-diameter fiber grating 7, $h_m$ is a thickness of the diaphragm 11, E is the modulus of elasticity of the elastomer 2, and A is a radial sectional area of the elastomer 2.

Assuming that the diaphragm undergoes a small deflection deformation under the action of the axial force Fz, considering only a bending deformation of the diaphragm in a vertical direction, a bending differential equation in polar coordinates may be obtained:

$$\frac{d}{dr}\left[\frac{1}{r}\frac{d}{dr}\left(r\frac{d\omega}{dr}\right)\right] = \frac{Pr}{2D},$$

where a bending stiffness of the diaphragm is $$D = \frac{E_1 h_m^3}{12(1-\mu^2)},$$

$\mu$ is a Poisson's ratio of the diaphragm 11; a load $$P = \frac{F_z}{A_m}$$

is applied, r is a boundary size of the diaphragm 11, substituting into a boundary condition:

$$\begin{cases} r = 0, & \dfrac{d\omega}{dr} = 0 \\ r = R, & \dfrac{d\omega}{dr} = 0, \omega = 0 \end{cases},$$

a maximum deflection $$\omega = \frac{3(1-\mu^2)R^4}{16\,E_1 h_m^3}P$$

generated by the center of the diaphragm is solved, and considering that there is the third through hole 300 at the center of the diaphragm, a boundary condition is taken as:

$$\begin{cases} r = r_w, & \dfrac{d\omega}{dr} = 0 \\ r = R, & \dfrac{d\omega}{dr} = 0, \omega = 0 \end{cases}.$$

A maximum deflection of the diaphragm is obtained as:

$$\omega_p = \frac{3(1-\mu^2)PR^4}{16 E_1 h_m^3}\left[1 - \left(\frac{r_w}{R}\right)^4 + 4\left(\frac{r_w}{R}\right)^2 \ln\frac{r_w}{R}\right],$$

where R is an outer diameter of the diaphragm 11; and $r_w$ is an outer diameter of the elastomer 2 between the two diaphragms 11.

The elastomer 2 uses a double-diaphragm structure. The outer cylinder and the inner cylinder generate a counterforce Fz on the diaphragms 12. According to a minimum deformation theory, the maximum deflection of the diaphragms 11 under action of the counterforce Fz is obtained as:

$$\omega_F = \frac{3(1-\mu^2)FzR^2}{4\pi E\,(h_m)^3}\left[1 - \left(\frac{r}{R}\right)^2 \frac{1 - \left(\frac{r}{R}\right)^2 + 4\ln^2\left(\frac{r}{R}\right)}{1 - \left(\frac{r}{R}\right)^2}\right];$$

In conjunction with the above, when the three-dimensional force sensor is only subjected to the action of the axial force Fz, strains of the suspended-tensioned sections of the three groups of etched stepped reduced-diameter fiber gratings 7 are obtained as $$\varepsilon_{Fz1} = \varepsilon_{Fz2} = \varepsilon_{Fz3} = \varepsilon_{Fz} = \frac{2\omega_p - 2\omega_F + \delta_z}{l}.$$

Then when the elastomer 2 is only subjected to the action of the axial force Fz, wavelength drifts corresponding to the normal sections and the etched stepped reduced-diameter sections of the three groups of etched stepped reduced-diameter fiber gratings 7 are:

$$\begin{cases} \Delta\lambda_{1-n} & = \dfrac{C}{1+C}\lambda_{1-n}(1-P_e)\varepsilon_{FZ} = K_{z1-n} \\ \Delta\lambda_{1-e} & = \dfrac{1}{1+C}\lambda_{1-e}(1-P_e)\varepsilon_{FZ} = K_{z1-e} \\ \Delta\lambda_{2-n} & = \dfrac{C}{1+C}\lambda_{2-n}(1-P_e)\varepsilon_{FZ} = K_{z2-n} \\ \Delta\lambda_{2-e} & = \dfrac{1}{1+C}\lambda_{2-e}(1-P_e)\varepsilon_{FZ} = K_{z2-e} \\ \Delta\lambda_{3-n} & = \dfrac{C}{1+C}\lambda_{3-n}(1-P_e)\varepsilon_{FZ} = K_{z3-n} \\ \Delta\lambda_{3-e} & = \dfrac{1}{1+C}\lambda_{3-e}(1-P_e)\varepsilon_{FZ} = K_{z3-e} \end{cases},$$

where $\Delta\lambda_{i-n}$ and $\Delta\lambda_{i-e}$ are wavelength drift amounts of central wavelengths generated by the normal section and the etched stepped reduced-diameter section of the suspended-tensioned etched stepped reduced-diameter fiber grating 7 respectively, $\lambda_{i-n}$ and $\lambda_{i-e}$ are initial central wavelengths of the normal section and the etched stepped reduced-diameter section of the suspended-tensioned etched stepped reduced-diameter fiber grating 7 respectively; a strain sensitivity ratio of the normal section and the etched stepped reduced-diameter section of the etched stepped reduced-diameter fiber grating 7 is $$C = \frac{l_4 + \dfrac{A_2}{A_1}(l - l_4)}{(l - l_4) + \dfrac{A_1}{A_2}l_4}; K_{zi-n}$$

and $K_{zi-e}$ are force sensitivities of the normal section and the etched stepped reduced-diameter section of the etched stepped reduced-diameter fiber grating 7 when the elastomer 2 is only subjected to the action of the axial force Fz; and $P_e$ is an effective elastic-optic constant of a fiber core of the optical fiber.

When the three-dimensional force sensor is subjected to action of the transverse force $F_X$, the elastomer 2 undergoes a transverse deformation, the first etched stepped reduced-diameter fiber grating 104 undergoes a deformation in a direction opposite to the second etched stepped reduced-diameter fiber grating 105, the deformation of the second etched stepped reduced-diameter fiber grating 105 is a half of the deformation of the first etched stepped reduced-diameter fiber grating 104; and the second etched stepped reduced-diameter fiber grating 105 undergoes a deformation of an equal magnitude and the same direction as that of the third etched stepped reduced-diameter fiber grating 106.

$$\varepsilon_{Fx2} = \varepsilon_{Fx3} = -\frac{\varepsilon_{Fx1}}{2}$$

is met, where $\varepsilon_{Fx1}$ is the deformation that occurs to the first etched stepped reduced-diameter fiber grating 104, $\varepsilon_{Fx2}$ is the deformation that occurs to the second etched stepped reduced-diameter fiber grating 105, and $\varepsilon_{Fx3}$ is the deformation that occurs to the third etched stepped reduced-diameter fiber grating 106.

When the three-dimensional force sensor is subjected to the action of the transverse force $F_X$, a displacement of a first curved connection portion 13 of the elastomer 2 in an x direction is:

$$\delta_{11} = F_x r_f \int_0^{l_1} \frac{h+x}{E_1 I_{l1} + E_f I_f} \, dx = \frac{F \chi r_f \left( h l_1 + \frac{1}{2} l_1^2 \right)}{E_1 I_{l1} + E_f I_f},$$

where $I_{l1}$ and $I_f$ are moments of inertia of the first curved connection portion 13 and the etched stepped reduced-diameter fiber grating 7 respectively; and h is a distance from a force bearing point of the transverse force to the adjacent diaphragm.

When the three-dimensional force sensor is subjected to the action of the transverse force $F_X$, a displacement of a first diaphragm of the elastomer 2 in the x direction is:

$$\delta_{12} = F_x r_f \int_0^{h_m} \frac{h+l_1+x}{E_1 I_m + E_f I_f} \, dx = \frac{F_x r_f \left[ (h+l_1)h_m + \frac{1}{2} h_m^2 \right]}{E_1 I_m + E_f I_f},$$

where $I_m$ is a moment of inertia of the diaphragm.

When the three-dimensional force sensor is subjected to the action of the transverse force $F_X$, a displacement of the double-layer cylinder 12 of the elastomer 2 in the x direction is:

$$\delta_{13} = F_x r_f \int_0^{l_2} \frac{h+l_1+h_m+x}{E_1 I_{l2} + E_f I_f} \, dx = \frac{F \chi r_f \left[ (h+l_1+h_m)l_2 + \frac{1}{2} l_2^2 \right]}{E_1 I_{l2} + E_f I_f},$$

where $I_{l2}$ is a moment of inertia of the double-layer cylinder 12.

When the three-dimensional force sensor is subjected to the action of the transverse force $F_X$, a displacement of a second diaphragm of the elastomer 2 in the x direction is:

$$\delta_{14} = F_x r_f \int_0^{h_m} \frac{h+l_1+h_m+l_2+x}{E_1 I_m + E_f I_f} \, dx =$$

-continued $$\frac{F_x r_f \left[ (h+l_1+h_m+l_2)h_m + \frac{1}{2} h_m^2 \right]}{E_1 I_m + E_f I_f}.$$

When the three-dimensional force sensor is subjected to the action of the transverse force $F_X$, a displacement of the first curved connection portion 13 of the elastomer 2 in the x direction is:

$$\delta_{15} =$$

$$F_x r_f \int_0^{l_1} \frac{h+l_1+2h_m+l_2+x}{E_1 I_{l1} + E_f I_f} \, dx = \frac{F_x r_f \left[ (h+l_1+2h_m+l_2)l_1 + \frac{1}{2} l_1^2 \right]}{E_1 I_{l1} + E_f I_f}.$$

According to a small deformation theory, a strain of the first suspended optical fiber may be obtained as: $\varepsilon_{Fx1}$, and $$\varepsilon_{Fx1} = \frac{\delta_{11}}{l_1} + \frac{\delta_{12}}{h_m} + \frac{\delta_{13}}{l_2} + \frac{\delta_{14}}{h_m} + \frac{\delta_{15}}{l_1} \text{ and } \varepsilon_{Fx2} = \varepsilon_{Fx3} = -\frac{\varepsilon_{Fx1}}{2}$$

are met. In combination with the above formula, $\varepsilon_{Fx1}$, $\varepsilon_{Fx2}$, and $\varepsilon_{Fx3}$ are derived.

Thus, when the three-dimensional force sensor is only subjected to the action of the axial force $F_X$, wavelength drifts corresponding to the normal sections and the etched stepped reduced-diameter sections of the three groups of etched stepped reduced-diameter fiber gratings 7 are:

$$\begin{cases} \Delta\lambda_{1-n} = \frac{C}{1+C}\lambda_{1-n}(1-P_e)\varepsilon_{Fx1} = K_{x1-n} \\ \Delta\lambda_{1-e} = \frac{1}{1+C}\lambda_{1-e}(1-P_e)\varepsilon_{Fx1} = K_{x1-e} \\ \Delta\lambda_{2-n} = \frac{C}{(1+C)}\lambda_{2-n}(1-P_e)\varepsilon_{Fx2} = K_{x2-n} \\ \Delta\lambda_{2-e} = \frac{1}{(1+C)}\lambda_{2-e}(1-P_e)\varepsilon_{Fx2} = K_{x2-e} \\ \Delta\lambda_{3-n} = \frac{C}{(1+C)}\lambda_{3-n}(1-P_e)\varepsilon_{Fx3} = K_{x3-n} \\ \Delta\lambda_{3-e} = \frac{1}{(1+C)}\lambda_{3-e}(1-P_e)\varepsilon_{Fx3} = K_{x3-e} \end{cases},$$

where $K_{xi-n}$ and $K_{xi-e}$ are force sensitivities of the normal section and the etched stepped reduced-diameter section of the etched stepped reduced-diameter fiber grating 7 when the elastomer 2 is only subjected to the action of the transverse force $F_X$.

When the three-dimensional force sensor is only subjected to action of the longitudinal force $F_y$, the elastomer 2 undergoes a longitudinal deformation, the first etched stepped reduced-diameter fiber grating 104 is located on a neutral layer, and the second etched stepped reduced-diameter fiber grating 105 undergoes a deformation of an equal magnitude and the same direction as that of the third etched stepped reduced-diameter fiber grating 106, such that deformations of the second etched stepped reduced-diameter fiber grating 105 and the third etched stepped reduced-diameter fiber grating 106 is $\varepsilon_{Fy2}$ $\varepsilon_{Fy2}$ and $\varepsilon_{Fy3}$ $\varepsilon_{Fy3}$ when the longitudinal force $F_y$ acts.

$$
\varepsilon_{Fy2} = -\frac{\sqrt{3}}{2}\left(
\frac{\dfrac{Fyr_f\left(hl_1+\frac{1}{2}l_1^2\right)}{E_1l_1+E_fl_f}}{l_1}
+ \frac{\dfrac{Fyr_f\left[(h+l_1)h_m+\frac{1}{2}h_m^2\right]}{E_1l_m+E_fl_f}}{h_m}
+ \frac{\dfrac{Fyr_f\left[(h+l_1+h_m)l_2+\frac{1}{2}l_2^2\right]}{E_1l_2+E_fl_f}}{l_2}
+ \frac{\dfrac{Fyr_f\left[(h+l_1+h_m+l_2)h_m+\frac{1}{2}h_m^2\right]}{E_1l_m+E_fl_f}}{h_m}
+ \frac{\dfrac{Fyr_f\left[(h+l_1+2h_m+l_2)l_1+\frac{1}{2}l_1^2\right]}{E_1l_1+E_fl_f}}{l_1}
\right)
$$

$$
\varepsilon_{Fy3} = \frac{\sqrt{3}}{2}\left(
\frac{\dfrac{Fyr_f\left(hl_1+\frac{1}{2}l_1^2\right)}{E_1l_1+E_fl_f}}{l_1}
+ \frac{\dfrac{Fyr_f\left[(h+l_1)h_m+\frac{1}{2}h_m^2\right]}{E_1l_m+E_fl_f}}{h_m}
+ \frac{\dfrac{Fyr_f\left[(h+l_1+h_m)l_2+\frac{1}{2}l_2^2\right]}{E_1l_2+E_fl_f}}{l_2}
+ \frac{\dfrac{Fyr_f\left[(h+l_1+h_m+l_2)h_m+\frac{1}{2}h_m^2\right]}{E_1l_m+E_fl_f}}{h_m}
+ \frac{\dfrac{Fyr_f\left[(h+l_1+2h_m+l_2)l_1+\frac{1}{2}l_1^2\right]}{E_1l_1+E_fl_f}}{l_1}
\right)
$$

Thus, when the three-dimensional force sensor is only subjected to the action of the longitudinal force $F_y$, wavelength drifts corresponding to the normal sections and the etched stepped reduced-diameter sections of the three groups of etched stepped reduced-diameter fiber gratings 7 are:

$$
\begin{cases}
\Delta\lambda_{1-n} = 0 \\
\Delta\lambda_{1-e} = 0 \\
\Delta\lambda_{2-n} = \dfrac{c}{(1+c)}\lambda_{2-n}(1-P_e)\varepsilon_{Fy2} = K_{y2-n} \\
\Delta\lambda_{2-e} = \dfrac{1}{(1+c)}\lambda_{2-e}(1-P_e)\varepsilon_{Fy2} = K_{y2-e} \\
\Delta\lambda_{3-n} = \dfrac{c}{(1+c)}\lambda_{3-n}(1-P_e)\varepsilon_{Fy3} = K_{y3-n} \\
\Delta\lambda_{3-e} = \dfrac{1}{(1+c)}\lambda_{3-e}(1-P_e)\varepsilon_{Fx3} = K_{y3-e}
\end{cases}
$$

where $K_{yi-n}$ and $K_{yi-e}$ are force sensitivities of the normal section and the etched stepped reduced-diameter section of the etched stepped reduced-diameter fiber grating 7 when the elastomer 2 is only subjected to the action of the longitudinal force.

When an ambient temperature changes, the central wavelength of the optical fiber drifts due to a thermo-optic effect of the optical fiber, a thermal expansion effect, and an elastic-optic effect caused by an internal thermal stress. Wavelength drifts corresponding to the normal sections and the etched stepped reduced-diameter sections of the three groups of etched stepped reduced-diameter fiber gratings 7 under an influence of the temperature are:

$$
\begin{cases}
\Delta\lambda_{t1-n} = C_T\lambda_{1-n}\Delta T = K_{T1-n} \\
\Delta\lambda_{t1-e} = C_T\lambda_{1-e}\Delta T = K_{T1-e} \\
\Delta\lambda_{t2-n} = C_T\lambda_{2-n}\Delta T = K_{T2-n} \\
\Delta\lambda_{t2-e} = C_T\lambda_{2-e}\Delta T = K_{T2-e} \\
\Delta\lambda_{t3-n} = C_T\lambda_{3-n}\Delta T = K_{T3-n} \\
\Delta\lambda_{t3-e} = C_T\lambda_{3-e}\Delta T = K_{T3-e}
\end{cases}
$$

where $\Delta\lambda_{ti-n}$ and $\Delta\lambda_{ti-e}$ are the wavelength drifts of the normal sections and the etched stepped reduced-diameter sections of the three groups of etched stepped reduced-diameter fiber gratings 7 under action of the temperature; a relative temperature sensitivity coefficient of the etched stepped reduced-diameter fiber grating 7 is $C_T=\zeta+\sigma$, $\zeta$ is a thermo-optic coefficient of the etched stepped reduced-diameter fiber grating 7, $\sigma$ is a linear thermal expansion coefficient of the etched stepped reduced-diameter fiber grating 7; $K_{Ti-n}$ and $K_{Ti-e}$ are temperature sensitivities of the normal section and the etched stepped reduced-diameter section of each etched stepped reduced-diameter fiber grating 7 respectively when the elastomer 2 is only subjected to the influence of the temperature.

Synthesizing the above cases where the force and the temperature act separately, a relationship matrix of the central wavelength drift amounts of reflectance spectra of the three groups of etched stepped reduced-diameter fiber gratings 7 and the three-dimensional force as well as the temperature is obtained as:

$$
\begin{bmatrix}
\Delta\lambda_{1-n} \\
\Delta\lambda_{1-e} \\
\Delta\lambda_{2-n} \\
\Delta\lambda_{2-e} \\
\Delta\lambda_{3-n} \\
\Delta\lambda_{3-e}
\end{bmatrix}
= \Delta\lambda_{6\times1} = K_{6\times4}
\begin{bmatrix}
F_x \\ F_y \\ F_z \\ \Delta T
\end{bmatrix}
=
\begin{bmatrix}
K_{x1-n} & 0 & K_{z1-n} & K_{T1-n} \\
K_{x1-e} & 0 & K_{z1-e} & K_{T1-e} \\
K_{x2-n} & K_{y2-n} & K_{z2-n} & K_{T2-n} \\
K_{x2-e} & K_{y2-e} & K_{z2-e} & K_{T2-e} \\
K_{x3-n} & K_{y3-n} & K_{z3-n} & K_{T3-n} \\
K_{x3-e} & K_{y3-e} & K_{z3-e} & K_{T3-e}
\end{bmatrix}
\begin{bmatrix}
F_x \\ F_y \\ F_z \\ \Delta T
\end{bmatrix},
$$

where $\Delta\lambda_{6\times1}$ is a central wavelength drift amount of the normal section and the etched stepped reduced-diameter section of each etched stepped reduced-diameter fiber grating 7, and $K_{6\times4}$ is a force and temperature sensitivity matrix.

S3: by solving a generalized inverse matrix of the force and temperature sensitivity matrix as a calibration matrix, central wavelength values of the three groups of etched stepped reduced-diameter fiber gratings 7 are decoupled to measure the three-dimensional force and the temperature.

Specifically, the three-dimensional force and the temperature $$
\begin{bmatrix}
F_x \\ F_y \\ F_z \\ \Delta T
\end{bmatrix}
= C_{4\times6}\cdot\Delta\lambda_{6\times1}
$$

are solved by solving the generalized inverse matrix $K_{6\times4}$ of the sensitivity matrix $C_{4\times6}$ as the calibration matrix, and through the central wavelength drift amount of the normal section and the etched stepped reduced-diameter section of each etched stepped reduced-diameter fiber grating (7).

S4: filtering three-dimensional force time series data, constructing a training sample, and using a long short-term memory (LSTM) neural network to train network parameters; and three-dimensional force data at a current moment are predicted and subsequent interaction force measurement data are recovered after training is completed, according to a sample corresponding to current input three-dimensional force data and in combination with historical fault-free three-dimensional force data and fault-free three-dimensional force data prior to the current moment, and a fault-tolerant output of three-dimensional force decoupling under a fault of the etched stepped reduced-diameter fiber gratings 7.

Figure 6:
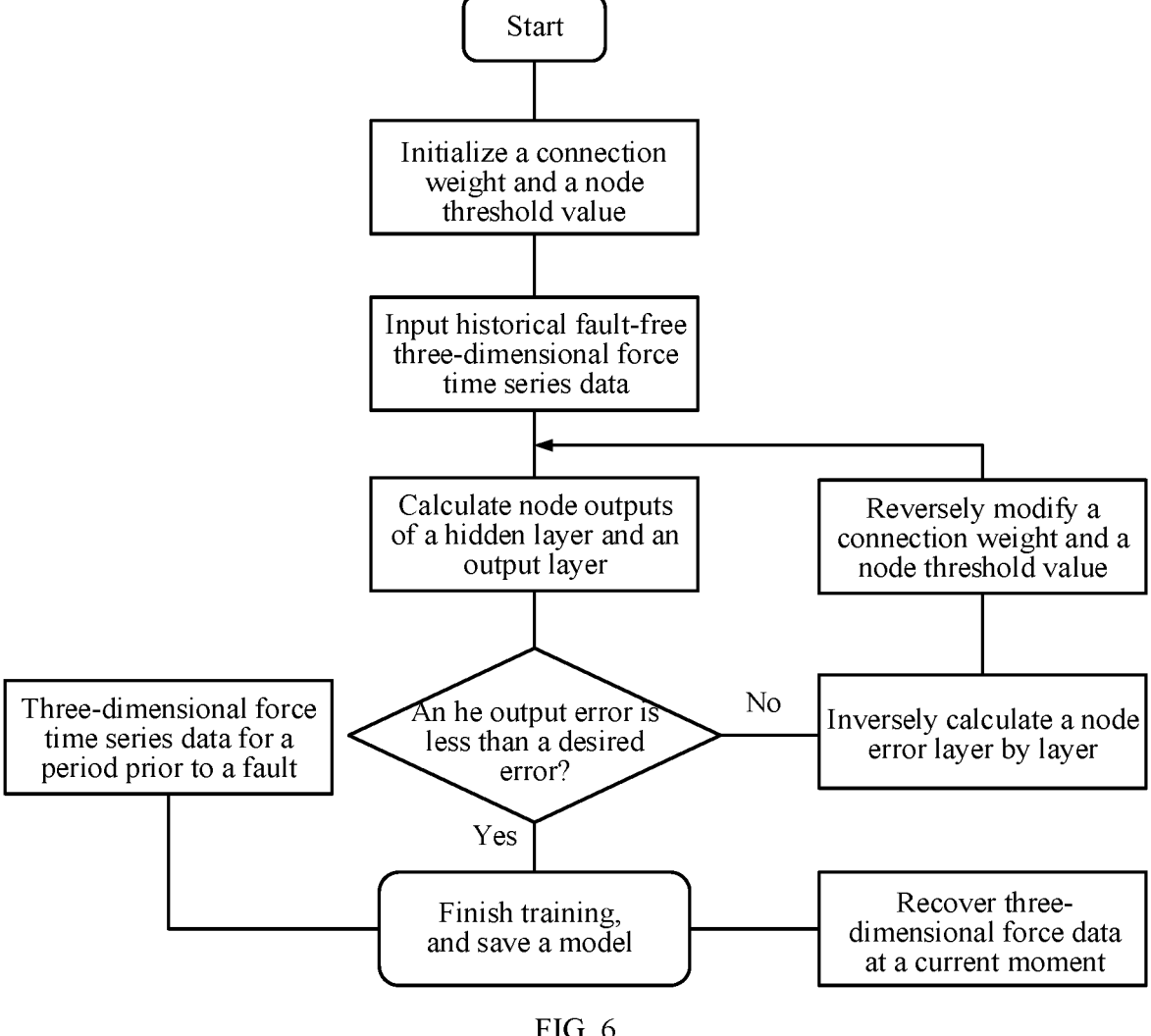
FIG. 6 is a flowchart of a data recovery of an LSTM network algorithm for a method for detecting a three-dimensional force of a fiber-integrated monolithic clamp guided by metal additive manufacturing of the present disclosure.

The content of step S4 is: using a Kalman filtering method to filter the historically measured three-dimensional force time series data of the three-dimensional force sensor, and normalizing the filtered three-dimensional force time series data; dividing the normalized three-dimensional force time series data into a training set and a test set, wherein the training set is used to establish a model, and the test set is used to verify a generalization ability of the model; and using a sliding time window to construct the training sample, building an LSTM neural network model, and using the training set to train parameters of the LSTM neural network model. As shown in FIG. 6, the figure shows a flowchart of inputting pre-fault three-dimensional force time series data to a trained LSTM network algorithm to recover three-dimensional force data at the current moment.

S5: types of the tissues clamped by the clamp are output in a classified manner through a random forest algorithm in combination with central wavelength drift amount information of the three groups of etched stepped reduced-diameter fiber gratings 7.

Figure 7:
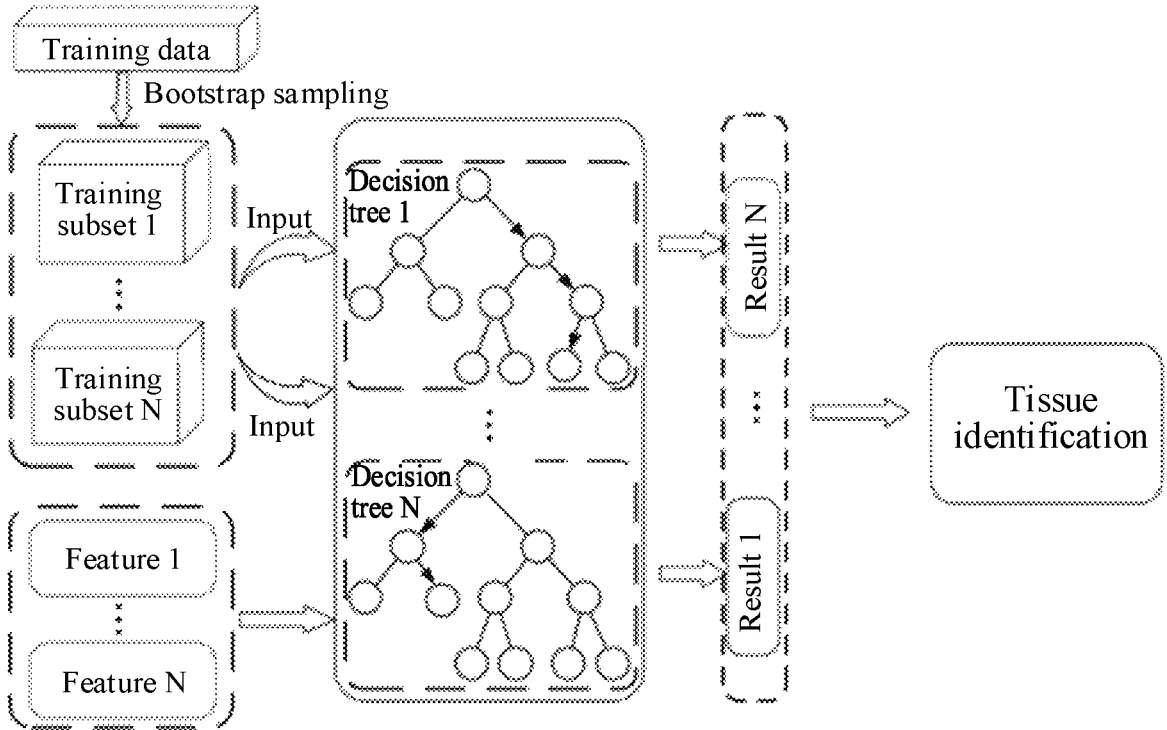
FIG. 7 is a flowchart of a tissue identification based on a random forest algorithm for a method for detecting a three-dimensional force of a fiber-integrated monolithic clamp guided by metal additive manufacturing of the present disclosure.

The content of step S5 is: using the random forest algorithm to classify the tissues clamped by the clamp head 1, as shown in FIG. 7, which provides a flowchart of a tissue identification based on the random forest algorithm; using the three-dimensional force obtained from a decoupling calculation as an input set of the random forest algorithm, using the types of the tissues as outputs, setting, in a training process of the random forest algorithm, the number of decision trees to be 100, a minimum number of leaves to be 1, and the number of candidate features for feature selection for each tree to be 2, using 70% of the input set as the training set, and using remaining 30% of the input set as the test set to verify the trained random forest algorithm.

The above describes the preferred embodiments of the present invention and is not intended to limit the present invention. Any modification, equivalent replacement, and improvement made within the spirit and scope of the present invention shall fall within the protection scope of the present invention.

What is claimed is:

1. A method for detecting a three-dimensional force of a fiber-integrated monolithic clamp guided by metal additive manufacturing, comprising the following steps:

S1: pre-preparing a three-dimensional force sensor, wherein the three-dimensional force sensor comprises a clamp head (1), an elastomer (2), and a transmission component, one end of the elastomer (2) in an axial direction is connected with the clamp head (1), and the clamp head (1) is configured to clamp tissues; another end of the elastomer (2) in the axial direction is provided with the transmission component, and the transmission component passes through the elastomer (2) to be in a transmission connection with the clamp head (1); and three groups of etched stepped reduced-diameter fiber gratings (7) are provided on the elastomer (2) in a centrosymmetric distribution;

S2: constructing, when the clamp head (1) of the three-dimensional force sensor clamps the tissues, a mechanical model of the elastomer (2), obtaining a strain of the elastomer (2) under action of the three-dimensional force, establishing, in combination with temperature sensitivity coefficients of the three groups of etched stepped reduced-diameter fiber gratings (7), a relationship between central wavelength drift amounts of the etched stepped reduced-diameter fiber gratings (7) and a temperature as well as the three-dimensional force, and deriving a force and temperature sensitivity matrix;

S3: decoupling, by solving a generalized inverse matrix of the force and temperature sensitivity matrix as a calibration matrix, central wavelength values of the three groups of etched stepped reduced-diameter fiber gratings (7) to measure the three-dimensional force and the temperature;

S4: filtering three-dimensional force time series data, constructing a training sample, and using a long short-term memory (LSTM) neural network to train network parameters; and predicting three-dimensional force data at a current moment and recovering subsequent interaction force measurement data after training is completed, according to a sample corresponding to current input three-dimensional force data and in combination with historical fault-free three-dimensional force data and fault-free three-dimensional force data prior to the current moment, and realizing a fault-tolerant output of three-dimensional force decoupling under a fault of the etched stepped reduced-diameter fiber gratings (7); and

S5: outputting types of the tissues clamped by the clamp in a classified manner through a random forest algorithm in combination with central wavelength drift amount information of the three groups of etched stepped reduced-diameter fiber gratings (7).

2. The method for detecting the three-dimensional force of a fiber-integrated monolithic clamp guided by metal additive manufacturing according to claim 1, wherein the elastomer (2) comprises a hollow double-layer cylinder (12), two diaphragms (11), and a plurality of curved connection portions; an inner cylinder is coaxially provided at an inner center of an outer cylinder of the double-layer cylinder (12), and two axially extending end portions of the inner cylinder are fixedly connected with two axially extending end portions of the outer cylinder respectively; an axially penetrating first through hole (100) is provided at centers of the end portions of the outer cylinder, and the first through hole (100) communicates with an interior of the inner cylinder: a plurality of penetrating second through holes (200) are formed on an end face located between an inner surface of the outer cylinder and an outer surface of the inner cylinder, and the second through holes (200) extend in an axial direction of the outer cylinder and are provided in a penetrating manner; the plurality of second through holes (200) are provided in centrosymmetry with respect to the first through hole (100);

the two diaphragms (11) are provided in a spaced manner on outer sides of the axially extending ends of the outer cylinder and spaced apart from the outer cylinder, a center of each of the two diaphragms (11) is provided with a penetrating third through hole (300), edges of the two diaphragms (11) are further provided with a plurality of optical fiber fixing holes (8), and the optical fiber fixing holes (8) are provided in a penetrating manner in the axial direction of the outer cylinder, and further extend outward in a radial direction of the diaphragms (11); the third through holes (300) and the first through hole (100) communicate with each other; the plurality of second through holes (200) and the plurality of optical fiber fixing holes (8) are provided in a one-to-one correspondence and mutual communication; and diameters of the two diaphragms (11) are approximately equal a diameter of the outer cylinder;

the plurality of curved connection portions are provided between the two diaphragms (11) and end faces of the outer cylinder, the curved connection portions are fixedly connected with the two diaphragms (11) and the outer cylinder respectively, one ends of the curved connection portions close to the outer cylinder are tangent to contours of the second through holes (200), and one ends of the curved connection portions away from the outer cylinder are flush with edges of the optical fiber fixing holes (8); inner surfaces of the plurality of curved connection portions are located on the same virtual cylinder, the virtual cylinder and the inner cylinder are coaxially provided, and a diameter of the virtual cylinder is larger than that of the first through hole (100), and the diameter of the virtual cylinder is smaller than an inner diameter of the outer cylinder;

the transmission component passes through the first through hole (100) and the third through holes (300) sequentially and is in a transmission connection with the clamp head (1); and the three groups of etched stepped reduced-diameter fiber gratings (7) pass through the optical fiber fixing holes (8) and the second through holes (200), and parts of the step reducing fiber gratings between the two diaphragms (11) are in a suspended-tensioned state, and a length of suspended and tensioned sections of the step reducing fiber gratings is the same as an axial length of the outer cylinder.

3. The method for detecting the three-dimensional force of a fiber-integrated monolithic clamp guided by metal additive manufacturing according to claim 2, wherein the three groups of etched stepped reduced-diameter fiber gratings (7) each comprise a metallized optical fiber, the metallized optical fiber is provided with a grating region, and the grating region comprises a normal section and a etched stepped reduced-diameter section provided sequentially; and metal nickel-plated layers are provided in a spaced manner at two ends of the grating region in an axially extending direction, and the metal nickel-plated layer is fixedly connected with an inner surface of the optical fiber fixing hole (8).

4. The method for detecting the three-dimensional force of a fiber-integrated monolithic clamp guided by metal additive manufacturing according to claim 3, wherein a method for preparing the elastomer (2) is: processing the outer cylinder, the inner cylinder, the two diaphragms (11), and the plurality of curved connection portions through a method of additive manufacturing of printing a titanium alloy powder, reserving a half of each of the second through holes (200) and the optical fiber fixing holes (8), afterwards, placing the etched stepped reduced-diameter fiber grating (7) in the correspondingly provided half of the second through hole (200) and optical fiber fixing hole (8), next preparing the complete second through hole (200) and optical fiber fixing hole (8) by laser scanning printing of the titanium alloy powder to fix the etched stepped reduced-diameter fiber grating (7), and then providing the three groups of etched stepped reduced-diameter fiber gratings (7) and the transmission component on the elastomer (2) sequentially in a penetrating manner.

5. The method for detecting the three-dimensional force of a fiber-integrated monolithic clamp guided by metal additive manufacturing according to claim 3, wherein step S2 is specified as:

the three-dimensional force sensor is affected by an axial force Fz, a transverse force $F_X$, a longitudinal force $F_y$, and the temperature;

when the three-dimensional force sensor is only subjected to action of the axial force Fz, strains of the suspended and tensioned sections of the three groups of etched stepped reduced-diameter fiber gratings (7) are: $\varepsilon_{Fz1}=\varepsilon_{Fz2}=\varepsilon_{Fz3}=\varepsilon_{Fz}$; then when the elastomer (2) is only subjected to the action of the axial force Fz, wavelength drifts corresponding to the normal sections and the etched stepped reduced-diameter sections of the three groups of etched stepped reduced-diameter fiber gratings (7) are:

$$
\begin{cases}
\Delta\lambda_{1-n} & = \dfrac{C}{1+C}\lambda_{1-n}(1-P_e)\varepsilon_{Fz} = K_{z1-n} \\[2mm]
\Delta\lambda_{1-e} & = \dfrac{1}{1+C}\lambda_{1-e}(1-P_e)\varepsilon_{Fz} = K_{z1-e} \\[2mm]
\Delta\lambda_{2-n} & = \dfrac{C}{1+C}\lambda_{2-n}(1-P_e)\varepsilon_{Fz} = K_{z2-n} \\[2mm]
\Delta\lambda_{2-e} & = \dfrac{1}{1+C}\lambda_{2-e}(1-P_e)\varepsilon_{Fz} = K_{z2-e} \\[2mm]
\Delta\lambda_{3-n} & = \dfrac{C}{1+C}\lambda_{3-n}(1-P_e)\varepsilon_{Fz} = K_{z3-n} \\[2mm]
\Delta\lambda_{3-e} & = \dfrac{1}{1+C}\lambda_{3-e}(1-P_e)\varepsilon_{Fz} = K_{z3-e}
\end{cases},
$$

where $\Delta\lambda_{i-n}$ and $\Delta\lambda_{i-e}$ are wavelength drift amounts of central wavelengths generated by the normal section and the etched stepped reduced-diameter section of the suspended-tensioned etched stepped reduced-diameter fiber grating (7) respectively, $\lambda_{i-n}$ and $\lambda_{i-e}$ are initial central wavelengths of the normal section and the etched stepped reduced-diameter section of the suspended-tensioned etched stepped reduced-diameter fiber grating (7) respectively, and i=1,2,3; C' is a strain sensitivity ratio of the normal section and the etched stepped reduced-diameter section of the etched stepped reduced-diameter fiber grating (7); $K_{zi-n}$ and $K_{zi-e}$ are force sensitivities of the normal section and the etched stepped reduced-diameter section of the etched stepped reduced-diameter fiber grating (7) when the elastomer (2) is only subjected to the action of the axial force Fz; and $P_e$ is an effective elastic-optic constant of a fiber core of the optical fiber;

when the three-dimensional force sensor is only subjected to action of the transverse force $F_X$; the elastomer (2) undergoes a transverse deformation, the three groups of etched stepped reduced-diameter fiber gratings (7) are named a first etched stepped reduced-diameter fiber grating, a second etched stepped reduced-diameter fiber grating, and a third etched stepped reduced-diameter fiber grating respectively; the first etched stepped reduced-diameter fiber grating undergoes a deformation in a direction opposite to the second etched stepped reduced-diameter fiber grating, and the deformation of the second etched stepped reduced-diameter fiber grating is a half of the deformation of the first etched stepped reduced-diameter fiber grating; the second etched stepped reduced-diameter fiber grating undergoes a deformation of an equal magnitude and the same direction as that of the third etched stepped reduced-diameter fiber grating, $$\varepsilon_{Fx2} = \varepsilon_{Fx3} = -\frac{\varepsilon_{Fx1}}{2}$$

is met, where $\varepsilon_{Fx1}$ is the deformation that occurs to the first etched stepped reduced-diameter fiber grating, $\varepsilon_{Fx2}$ is the deformation that occurs to the second etched stepped reduced-diameter fiber grating, and $\varepsilon_{Fx3}$ is the deformation that occurs to the third etched stepped reduced-diameter fiber grating; thus, when the elastomer (2) is only subjected to the action of the axial force $F_X$, wavelength drifts corresponding to the normal sections and the etched stepped reduced-diameter sections of the three groups of etched stepped reduced-diameter fiber gratings (7) are:

$$\begin{cases} \Delta\lambda_{1-n} &= \frac{c}{1+C}\lambda_{1-n}(1-P_e)\varepsilon_{Fx1} = K_{x1-n} \\ \Delta\lambda_{1-e} &= \frac{1}{1+C}\lambda_{1-c}(1-P_e)\varepsilon_{Fx1} = K_{x1-e} \\ \Delta\lambda_{2-n} &= \frac{c}{(1+C)}\lambda_{2-n}(1-P_e)\varepsilon_{Fx2} = K_{x2-n} \\ \Delta\lambda_{2-e} &= \frac{1}{(1+C)}\lambda_{2-e}(1-P_e)\varepsilon_{Fx2} = K_{x2-e} \\ \Delta\lambda_{3-n} &= \frac{c}{(1+C)}\lambda_{3-n}(1-P_c)\varepsilon_{Fx3} = K_{x3-n} \\ \Delta\lambda_{3-e} &= \frac{1}{(1+C)}\lambda_{3-e}(1-P_e)E_{Fx3} = K_{x3-e} \end{cases},$$

where $K_{xi-n}$ and $K_{xi-e}$ are force sensitivities of the normal section and the etched stepped reduced-diameter section of the etched stepped reduced-diameter fiber grating (7) when the elastomer (2) is only subjected to the action of the transverse force $F_X$;

when the three-dimensional force sensor is only subjected to action of the longitudinal force $F_y$, the elastomer (2) undergoes a longitudinal deformation, the first etched stepped reduced-diameter fiber grating is located on a neutral layer, the second etched stepped reduced-diameter fiber grating undergoes a deformation of an equal magnitude and an opposite direction to the third etched stepped reduced-diameter fiber grating, such that deformations of the second etched stepped reduced-diameter fiber grating and the third etched stepped reduced-diameter fiber grating are $\varepsilon_{Fy2}$ and $\varepsilon_{Fy3}$ when the longitudinal force $F_y$ acts, then when the elastomer (2) is only subjected to the action of the longitudinal force $F_y$, wavelength drifts corresponding to the normal sections and the etched stepped reduced-diameter sections of the three groups of etched stepped reduced-diameter fiber gratings (7) are:

$$\begin{cases} \Delta\lambda_{1-n} = 0 \\ \Delta\lambda_{1-e} = 0 \\ \Delta\lambda_{2-n} = \frac{c}{(1+C)}\lambda_{2-n}(1-P_e)\varepsilon_{Fy2} = K_{y2-n} \\ \Delta\lambda_{2-e} = \frac{1}{(1+C)}\lambda_{2-e}(1-P_e)\varepsilon_{Fy2} = K_{y2-e} \\ \Delta\lambda_{3-n} = \frac{c}{(1+C)}\lambda_{3-n}(1-P_e)\varepsilon_{Fy3} = K_{y3-n} \\ \Delta\lambda_{3-e} = \frac{1}{(1+C)}\lambda_{3-e}(1-P_e)\varepsilon_{Fx3} = K_{y3-e} \end{cases},$$

where $K_{yi-n}$ and $K_{yi-e}$ are force sensitivities of the normal section and the etched stepped reduced-diameter section of the etched stepped reduced-diameter fiber grating (7) when the elastomer (2) is only subjected to the action of the longitudinal force $F_y$;

when an ambient temperature changes, a central wavelength of the optical fiber drifts due to a thermo-optic effect of the optical fiber, a thermal expansion effect, and an elastic-optic effect caused by an internal thermal stress, and wavelength drifts corresponding to the normal sections and the etched stepped reduced-diameter sections of the three groups of etched stepped reduced-diameter fiber gratings (7) under an influence of the temperature are:

$$\begin{cases} \Delta\lambda_{t1-n} &= C_T\lambda_{1-n}\Delta T = K_{T1-n} \\ \Delta\lambda_{t1-e} &= C_T\lambda_{1-e}\Delta T = K_{T1-e} \\ \Delta\lambda_{t2-n} &= C_T\lambda_{2-n}\Delta T = K_{T2-n} \\ \Delta\lambda_{t2-e} &= C_T\lambda_{2-e}\Delta T = K_{T2-e} \\ \Delta\lambda_{t3-n} &= C_T\lambda_{3-n}\Delta T = K_{T3-n} \\ \Delta\lambda_{t3-e} &= C_T\lambda_{3-e}\Delta T = K_{T3-e} \end{cases},$$

where $\Delta\lambda_{ti-n}$ and $\Delta\lambda_{ti-e}$ are the wavelength drifts of the normal sections and the etched stepped reduced-diameter sections of the three groups of etched stepped reduced-diameter fiber gratings (7) under action of the temperature; a relative temperature sensitivity coefficient of the etched stepped reduced-diameter fiber grating (7) is $C_T=\zeta+\sigma$, $\zeta$ is a thermo-optic coefficient of the etched stepped reduced-diameter fiber grating (7), and o is a linear thermal expansion coefficient of the etched stepped reduced-diameter fiber grating (7); $K_{Ti-n}$ and $K_{Ti-e}$ are temperature sensitivities of the normal section and the etched stepped reduced-diameter section of each etched stepped reduced-diameter fiber grating (7) respectively when the elastomer (2) is only subjected to the influence of the temperature; and synthesizing the above cases where the force and the temperature act separately, a relationship matrix of the central wavelength drift amounts of reflectance spectra of the three groups of etched stepped reduced-diameter fiber gratings (7) and the three-dimensional force as well as the temperature is obtained as:

$$\begin{bmatrix} \Delta\lambda_{1-n} \\ \Delta\lambda_{1-e} \\ \Delta\lambda_{2-n} \\ \Delta\lambda_{2-e} \\ \Delta\lambda_{3-n} \\ \Delta\lambda_{3-e} \end{bmatrix} = \Delta\lambda_{6\times1} = K_{6\times4}\begin{bmatrix} F_x \\ F_y \\ F_z \\ \Delta T \end{bmatrix} = \begin{bmatrix} K_{x1-n} & 0 & K_{z1-n} & K_{T1-n} \\ K_{x1-e} & 0 & K_{z1-e} & K_{T1-e} \\ K_{x2-n} & K_{y2-n} & K_{z2-n} & K_{T2-n} \\ K_{x2-e} & K_{y2-e} & K_{z2-e} & K_{T2-e} \\ K_{x3-n} & K_{y3-n} & K_{z3-n} & K_{T3-n} \\ K_{x3-e} & K_{y3-e} & K_{z3-e} & K_{T3-e} \end{bmatrix}\begin{bmatrix} F_x \\ F_y \\ F_z \\ \Delta T \end{bmatrix},$$

where $\Delta\lambda_{6\times1}$ is a central wavelength drift amount of the normal section and the etched stepped reduced-diameter section of each etched stepped reduced-diameter fiber grating (7), and $K_{6\times4}$ is the force and temperature sensitivity matrix.

6. The method for detecting the three-dimensional force of a fiber-integrated monolithic clamp guided by metal additive manufacturing according to claim 5, wherein a content of step S3 is: solving the three-dimensional force and the temperature $$\begin{bmatrix} F_x \\ F_y \\ F_z \\ \Delta T \end{bmatrix} = C_{4\times6} \cdot \Delta\lambda_{6\times1}$$

by solving the generalized inverse matrix $C_{4\times6}$ of the sensitivity matrix $K_{6\times4}$ as the calibration matrix, and through the central wavelength drift amount $\Delta\lambda_{6\times1}$ of the normal section and the etched stepped reduced-diameter section of each etched stepped reduced-diameter fiber grating (7).

7. The method for detecting the three-dimensional force of a fiber-integrated monolithic clamp guided by metal additive manufacturing according to claim 6, wherein The content of step S4 is: using a Kalman filtering method to filter the historically measured three-dimensional force time series data of the three-dimensional force sensor, and normalizing the filtered three-dimensional force time series data; dividing the normalized three-dimensional force time series data into a training set and a test set, wherein the training set is used to establish a model, and the test set is used to verify a generalization ability of the model; and using a sliding time window to construct the training sample, building an LSTM neural network model, and using the training set to train parameters of the LSTM neural network model.

8. The method for detecting the three-dimensional force of a fiber-integrated monolithic clamp guided by metal additive manufacturing according to claim 7, wherein a content of step S5 is: using the random forest algorithm to classify the tissues clamped by the clamp head (1), using the three-dimensional force obtained from a decoupling calculation as an input set of the random forest algorithm, using the types of the tissues as outputs, setting, in a training process of the random forest algorithm, the number of decision trees to be 100, a minimum number of leaves to be 1, and the number of candidate features for feature selection for each tree to be 2, using 70% of the input set as the training set, and using remaining 30% of the input set as the test set to verify the trained random forest algorithm.

9. The method for detecting the three-dimensional force of a fiber-integrated monolithic clamp guided by metal additive manufacturing according to claim 3, wherein a diameter of the etched stepped reduced-diameter fiber grating (7) is 125 μm, a length of the grating region is 3 mm, and the normal section and the etched stepped reduced-diameter section each contain a half of the grating region.

*  *  *  *  *